USO10589067B2

(12) United States Patent
Ciccone

(10) Patent No.: US 10,589,067 B2
(45) Date of Patent: *Mar. 17, 2020

(54) MEDICAL DEVICE SECUREMENT SYSTEM

(71) Applicant: C. R. BARD, INC., Covington, GA (US)

(72) Inventor: Paul Ciccone, Social Circle, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1218 days.

This patent is subject to a terminal disclaimer.

(21) Appl. No.: 14/285,460

(22) Filed: May 22, 2014

(65) Prior Publication Data

US 2014/0276542 A1 Sep. 18, 2014

Related U.S. Application Data

(63) Continuation of application No. 12/666,272, filed as application No. PCT/US2009/057566 on Sep. 18, 2009, now Pat. No. 8,734,400.

(Continued)

(51) Int. Cl.
*A61M 25/02* (2006.01)

(52) U.S. Cl.
CPC ....... *A61M 25/02* (2013.01); *A61M 2025/024* (2013.01); *A61M 2025/0266* (2013.01)

(58) Field of Classification Search
CPC ............ A61M 25/02; A61M 2025/024; A61M 2025/026
See application file for complete search history.

(56) References Cited

U.S. PATENT DOCUMENTS 2,525,398 A * 10/1950 Collins ................... A61M 5/00
128/DIG. 26
2,533,961 A 12/1950 Rousseau et al.
(Continued)

FOREIGN PATENT DOCUMENTS

CA   1 311 977    12/1992
CA   1 318 824    6/1993
(Continued)

OTHER PUBLICATIONS

CA 2,737,640 filed Sep. 18, 2012 First Office Action dated Sep. 24, 2015.
(Continued)

*Primary Examiner* — Bradley J Osinski
*Assistant Examiner* — Matthew A Engel
(74) *Attorney, Agent, or Firm* — Rutan & Tucker LLP

(57) ABSTRACT

A catheter securement device holds a medical article such as a catheter in position upon the body of a patient and at least inhibits longitudinal movement of the medical article. The securement device includes a retainer and a clamp. The retainer and clamp include interengaging structure. The interengaging structure may be a ratchet mechanism by which a medical provider tightens the clamp against the retainer. The ratchet mechanism allows a single securement system to be used with medical articles that have different longitudinal lengths as well as medical articles that have distally located contact surfaces. The retainer forms a channel into which at least a portion of the medical article is inserted. Each of the retainer and the clamp include at least one abutment surface that can abut against a contact point or surface on the medical article. The abutments inhibit motion of the medical article in proximal and distal directions through the channel when the clamp is tightened against the (Continued)

retainer. The securement system may be designed for single or multi-use.

12 Claims, 36 Drawing Sheets

Related U.S. Application Data

(60) Provisional application No. 61/098,704, filed on Sep. 19, 2008.

(56) References Cited

U.S. PATENT DOCUMENTS

| | | | |
|---|---|---|---|
| 2,707,953 A | 5/1955 | Ryan | |
| 3,046,984 A | 7/1962 | Eby | |
| 3,059,645 A | 10/1962 | Hasbrouck et al. | |
| 3,064,648 A | 11/1962 | Bujan | |
| 3,167,072 A | 1/1965 | Stone et al. | |
| 3,194,235 A | 7/1965 | Cooke | |
| 3,288,137 A | 11/1966 | Lund | |
| 3,482,569 A | 12/1969 | Raffaelli | |
| 3,602,227 A * | 8/1971 | Andrew | A61M 25/02 128/207.17 |
| 3,613,663 A | 10/1971 | Johnson | |
| 3,630,195 A | 12/1971 | Santomieri | |
| 3,677,250 A | 7/1972 | Thomas | |
| 3,766,915 A | 10/1973 | Rychlik | |
| 3,782,383 A | 1/1974 | Thompson et al. | |
| 3,826,254 A | 7/1974 | Mellor | |
| 3,834,380 A | 9/1974 | Boyd | |
| 3,856,020 A | 12/1974 | Kovac | |
| 3,863,527 A | 2/1975 | Berning | |
| 3,896,527 A | 2/1975 | Berning | |
| 3,900,026 A | 8/1975 | Wagner | |
| 3,901,226 A | 8/1975 | Scardenzan | |
| 3,906,946 A | 9/1975 | Nordström | |
| 3,973,565 A | 8/1976 | Steer | |
| 4,003,227 A * | 1/1977 | Casey | E05B 13/002 292/258 |
| 4,020,835 A | 5/1977 | Nordstrom et al. | |
| 4,057,066 A | 11/1977 | Taylor | |
| 4,059,105 A | 11/1977 | Cutruzzula et al. | |
| 4,082,094 A | 4/1978 | Dailey | |
| 4,129,128 A | 12/1978 | McFarlane | |
| 4,142,527 A | 3/1979 | Garcia | |
| 4,161,177 A | 7/1979 | Fuchs | |
| 4,165,748 A | 8/1979 | Johnson | |
| D252,822 S * | 9/1979 | McFarlane | D24/128 |
| 4,193,174 A | 3/1980 | Stephens | |
| 4,224,937 A | 9/1980 | Gordon | |
| 4,248,229 A | 2/1981 | Miller | |
| 4,250,880 A | 2/1981 | Gordon | |
| 4,275,143 A | 6/1981 | Olson | |
| 4,275,721 A | 6/1981 | Olson | |
| 4,284,076 A | 8/1981 | Hall | |
| 4,316,461 A | 2/1982 | Marais et al. | |
| 4,326,519 A | 4/1982 | D'Alo et al. | |
| 4,333,468 A | 6/1982 | Geist | |
| 4,362,156 A | 12/1982 | Feller et al. | |
| 4,392,853 A | 7/1983 | Muto | |
| 4,397,647 A | 8/1983 | Gordon | |
| 4,449,975 A | 5/1984 | Perry | |
| 4,453,933 A | 6/1984 | Speaker | |
| 4,470,410 A | 9/1984 | Elliott | |
| 4,480,639 A | 11/1984 | Peterson et al. | |
| 4,484,913 A | 11/1984 | Swauger | |
| 4,516,968 A | 5/1985 | Marshall et al. | |
| 4,517,971 A | 5/1985 | Sorbonne | |
| 4,563,177 A | 1/1986 | Kamen | |
| 4,627,842 A | 12/1986 | Katz | |
| 4,632,670 A | 12/1986 | Muller | |
| 4,633,863 A | 1/1987 | Filips et al. | |
| 4,645,492 A | 2/1987 | Weeks | |
| 4,669,458 A | 6/1987 | Abraham et al. | |
| 4,683,882 A | 8/1987 | Laird | |
| 4,699,616 A * | 10/1987 | Nowak | A61M 25/02 128/DIG. 26 |
| 4,711,636 A | 12/1987 | Bierman | |
| 4,737,143 A | 4/1988 | Russell | |
| 4,742,824 A | 5/1988 | Payton et al. | |
| 4,752,292 A * | 6/1988 | Lopez | A61M 39/1011 604/244 |
| 4,792,163 A * | 12/1988 | Kulle | A61M 39/1011 108/44 |
| 4,808,162 A | 2/1989 | Oliver | |
| 4,822,342 A | 4/1989 | Brawner | |
| 4,826,486 A | 5/1989 | Palsrok et al. | |
| 4,832,019 A | 5/1989 | Weinstein et al. | |
| 4,846,807 A | 7/1989 | Safadago | |
| 4,852,844 A | 8/1989 | Villaveces | |
| 4,857,058 A | 8/1989 | Payton | |
| 4,863,432 A | 9/1989 | Kvalo | |
| 4,897,082 A | 1/1990 | Erskine | |
| 4,898,587 A | 2/1990 | Mera | |
| 4,903,995 A * | 2/1990 | Blenkush | F16L 33/225 285/255 |
| 4,919,654 A | 4/1990 | Kalt | |
| 4,921,199 A | 5/1990 | Villaveces | |
| 4,955,864 A | 9/1990 | Hajduch | |
| 4,976,698 A | 12/1990 | Stokley | |
| 4,976,700 A | 12/1990 | Tollini | |
| 4,981,475 A | 1/1991 | Haindl | |
| 4,986,815 A | 1/1991 | Schneider | |
| 4,997,421 A | 3/1991 | Palsrok et al. | |
| 5,037,397 A | 8/1991 | Kalt et al. | |
| 5,069,206 A | 12/1991 | Crosbie | |
| 5,073,170 A | 12/1991 | Schneider | |
| 5,074,847 A | 12/1991 | Greenwell et al. | |
| 5,084,026 A | 1/1992 | Shapiro | |
| 5,098,399 A | 3/1992 | Tollini | |
| 5,112,313 A | 5/1992 | Sallee | |
| 5,116,324 A | 5/1992 | Brierley et al. | |
| 5,135,505 A * | 8/1992 | Kaufman | A61M 25/0631 604/165.02 |
| 5,137,519 A | 8/1992 | Littrell et al. | |
| 5,147,322 A | 9/1992 | Bowen et al. | |
| 5,156,641 A | 10/1992 | White | |
| 5,167,630 A | 12/1992 | Paul | |
| 5,192,273 A * | 3/1993 | Bierman | A61M 25/02 604/174 |
| 5,192,274 A | 3/1993 | Bierman | |
| 5,195,981 A | 3/1993 | Johnson | |
| 5,215,531 A * | 6/1993 | Maxson | A61M 25/02 128/DIG. 26 |
| 5,215,532 A | 6/1993 | Atkinson | |
| 5,236,421 A | 8/1993 | Becher | |
| 5,238,010 A | 8/1993 | Grabenkort | |
| 5,266,401 A | 11/1993 | Tollini | |
| 5,267,967 A * | 12/1993 | Schneider | A61M 25/02 128/DIG. 6 |
| 5,290,248 A * | 3/1994 | Bierman | A61M 39/1011 604/174 |
| 5,292,312 A | 3/1994 | Delk et al. | |
| 5,304,146 A | 4/1994 | Johnson et al. | |
| 5,306,243 A | 4/1994 | Bonaldo | |
| D347,060 S | 5/1994 | Bierman | |
| 5,314,411 A * | 5/1994 | Bierman | A61M 25/02 604/174 |
| 5,322,097 A | 6/1994 | Wright | |
| 5,328,487 A | 7/1994 | Starchevich | |
| 5,338,308 A | 8/1994 | Wilk | |
| 5,338,313 A * | 8/1994 | Mollenauer | A61M 39/0613 251/4 |
| 5,342,317 A | 8/1994 | Claywell | |
| 5,344,406 A | 9/1994 | Spooner | |
| 5,352,211 A | 10/1994 | Merskelly | |
| 5,354,282 A | 10/1994 | Bierman | |
| 5,356,391 A | 10/1994 | Stewart | |
| 5,370,627 A | 12/1994 | Conway | |
| 5,372,589 A | 12/1994 | Davis | |
| 5,380,293 A | 1/1995 | Grant | |
| 5,380,395 A | 1/1995 | Uchida | |

(56) References Cited

U.S. PATENT DOCUMENTS

| | | |
|---|---|---|
| 5,382,239 A | 1/1995 | Orr et al. |
| 5,395,344 A | 3/1995 | Beisang et al. |
| 5,402,776 A | 4/1995 | Islava |
| 5,403,285 A | 4/1995 | Roberts |
| 5,413,120 A | 5/1995 | Grant |
| 5,413,562 A * | 5/1995 | Swauger ............... A61M 25/02 128/DIG. 26 |
| D359,120 S | 6/1995 | Sallee et al. |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,480,719 A | 1/1996 | Tollini |
| 5,496,282 A | 3/1996 | Militzer et al. |
| 5,496,283 A | 3/1996 | Alexander |
| 5,499,976 A | 3/1996 | Dalton |
| 5,514,109 A * | 5/1996 | Mollenauer ....... A61M 39/0613 251/4 |
| 5,520,656 A | 5/1996 | Byrd |
| 5,527,293 A | 6/1996 | Zamierowski |
| 5,549,567 A | 8/1996 | Wolman |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| 5,593,395 A | 1/1997 | Martz |
| D377,831 S | 2/1997 | Bierman |
| 5,605,546 A | 2/1997 | Wolzinger et al. |
| 5,637,098 A | 6/1997 | Bierman |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,755,225 A | 5/1998 | Hutson |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,254 A | 3/1999 | Matyas |
| 5,897,519 A | 4/1999 | Shesol et al. |
| 5,911,707 A | 6/1999 | Wolvek et al. |
| 5,916,200 A | 6/1999 | Eppley et al. |
| 5,947,931 A | 9/1999 | Bierman |
| 6,050,934 A | 4/2000 | Mikhail et al. |
| D425,619 S | 5/2000 | Bierman |
| 6,067,985 A | 5/2000 | Islava |
| 6,099,509 A | 8/2000 | Brown et al. |
| 6,113,577 A | 9/2000 | Hakky et al. |
| 6,132,398 A | 10/2000 | Bierman |
| 6,132,399 A | 10/2000 | Shultz |
| 6,213,979 B1 | 4/2001 | Bierman |
| 6,224,571 B1 * | 5/2001 | Bierman ............... A61M 25/02 604/174 |
| 6,228,064 B1 | 5/2001 | Abita et al. |
| 6,231,547 B1 | 5/2001 | O'Hara |
| 6,231,548 B1 * | 5/2001 | Bassett ............... A61M 25/02 128/DIG. 26 |
| 6,258,066 B1 | 6/2001 | Urich |
| 6,283,945 B1 | 9/2001 | Bierman |
| 6,287,281 B1 | 9/2001 | Nishtala et al. |
| 6,290,676 B1 | 9/2001 | Bierman |
| 6,361,523 B1 | 3/2002 | Bierman |
| 6,375,639 B1 | 4/2002 | Duplessie |
| 6,413,240 B1 | 7/2002 | Bierman et al. |
| 6,428,515 B1 * | 8/2002 | Bierman ............... A61M 25/02 128/DIG. 26 |
| 6,428,516 B1 | 8/2002 | Bierman et al. |
| 6,436,073 B1 | 8/2002 | Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch |
| 6,488,664 B1 | 12/2002 | Solomon et al. |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,516,498 B2 * | 2/2003 | LaCoy ................ F16L 3/1025 24/16 R |
| 6,517,522 B1 * | 2/2003 | Bell ................ A61M 25/0637 604/165.02 |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell |
| 6,626,890 B2 | 9/2003 | Nguyen et al. |
| 6,652,487 B1 | 11/2003 | Cook |
| 6,663,600 B2 | 12/2003 | Bierman et al. |
| 6,689,104 B2 | 2/2004 | Bierman |
| D492,411 S | 6/2004 | Bierman |
| 6,743,210 B2 * | 6/2004 | Hart ................... A61F 2/95 604/194 |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 * | 12/2004 | Tollini ................ A61M 25/02 128/DIG. 26 |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman |
| 7,070,580 B2 | 7/2006 | Nielsen |
| 7,090,660 B2 | 8/2006 | Roberts et al. |
| D528,206 S | 9/2006 | Bierman |
| 7,153,291 B2 | 12/2006 | Bierman |
| 7,354,421 B2 | 4/2008 | Bierman |
| 7,377,472 B2 * | 5/2008 | Brown ................ F16L 3/10 24/16 R |
| 7,413,561 B2 | 8/2008 | Raulerson et al. |
| 7,794,387 B2 * | 9/2010 | Olson ................ A61B 17/02 600/37 |
| 7,799,001 B2 | 9/2010 | Bierman |
| 8,105,290 B2 * | 1/2012 | Wright ................ A61M 25/02 604/174 |
| 8,162,898 B1 * | 4/2012 | Wright ................ A61M 5/158 24/269 |
| 8,211,063 B2 * | 7/2012 | Bierman ............... A61M 25/02 604/174 |
| 8,251,956 B2 * | 8/2012 | Bierman ............... A61M 25/02 604/174 |
| 8,357,124 B2 | 1/2013 | Bierman |
| 8,657,791 B2 * | 2/2014 | Bierman ............... A61M 5/1415 604/174 |
| 8,734,400 B2 | 5/2014 | Ciccone |
| 8,740,852 B2 | 6/2014 | Aviles |
| 9,415,191 B2 | 8/2016 | Aviles |
| 9,561,348 B2 | 2/2017 | Bierman |
| 2001/0011164 A1 | 8/2001 | Bierman |
| 2002/0068904 A1 | 6/2002 | Bierman et al. |
| 2002/0099360 A1 | 7/2002 | Bierman |
| 2002/0133121 A1 | 9/2002 | Bierman |
| 2003/0055382 A1 | 3/2003 | Schaeffer |
| 2003/0229313 A1 | 12/2003 | Bierman |

(56) References Cited

U.S. PATENT DOCUMENTS

| | | | |
|---|---|---|---|
| 2004/0102736 A1* | 5/2004 | Bierman | A61M 25/02 604/180 |
| 2004/0111067 A1 | 6/2004 | Kirchhofer | |
| 2004/0138624 A1 | 7/2004 | Bierman | |
| 2004/0204685 A1* | 10/2004 | Wright | A61M 25/02 604/174 |
| 2005/0182367 A1 | 8/2005 | Walborn | |
| 2005/0215953 A1 | 9/2005 | Rossen | |
| 2005/0251157 A1 | 11/2005 | Saadat et al. | |
| 2005/0288635 A1 | 12/2005 | Davis et al. | |
| 2006/0015076 A1 | 1/2006 | Heinzerling et al. | |
| 2006/0064063 A1 | 3/2006 | Bierman | |
| 2006/0135944 A1 | 6/2006 | Bierman | |
| 2006/0184127 A1* | 8/2006 | Bierman | A61M 25/02 604/177 |
| 2006/0184129 A1* | 8/2006 | Bierman | A61M 25/02 604/180 |
| 2006/0217669 A1 | 9/2006 | Botha | |
| 2006/0247577 A1* | 11/2006 | Wright | A61M 5/158 604/174 |
| 2006/0264836 A1 | 11/2006 | Bierman | |
| 2006/0270995 A1 | 11/2006 | Bierman | |
| 2007/0173766 A1 | 7/2007 | Bierman | |
| 2008/0125718 A1 | 5/2008 | Tsuchiya et al. | |
| 2008/0132848 A1 | 6/2008 | Wright et al. | |
| 2009/0143740 A1* | 6/2009 | Bierman | A61M 5/1415 604/177 |
| 2010/0179482 A1 | 7/2010 | Wright et al. | |
| 2010/0324491 A1* | 12/2010 | Bierman | A61M 25/02 604/174 |
| 2011/0245866 A1* | 10/2011 | Cassingham | A61B 17/00491 606/213 |
| 2011/0282291 A1* | 11/2011 | Ciccone | A61M 25/02 604/178 |

FOREIGN PATENT DOCUMENTS

| | | |
|---|---|---|
| EP | 0064284 A2 | 11/1982 |
| EP | 356683 A1 | 3/1990 |
| EP | 2470251 B1 | 12/2014 |
| FR | 2381529 | 2/1978 |
| FR | 2922458 A1 | 4/2009 |
| GB | 2086466 | 5/1982 |
| GB | 2211417 | 7/1989 |
| GB | 2211417 A | 7/1989 |
| WO | WO 80/01458 | 7/1980 |
| WO | WO 94/12231 | 6/1994 |
| WO | 9421319 A1 | 9/1994 |
| WO | 9715337 A1 | 5/1997 |
| WO | 9955409 A1 | 11/1999 |
| WO | 00/48658 A1 | 8/2000 |
| WO | 2004016309 A2 | 2/2004 |
| WO | 2004022140 A1 | 3/2004 |
| WO | 2007024900 A2 | 3/2007 |
| WO | WO 2007/117655 A2 | 10/2007 |
| WO | WO 08/151047 A1 | 12/2008 |
| WO | 2011025478 A1 | 3/2011 |
| WO | 2011133818 A1 | 10/2011 |

OTHER PUBLICATIONS

PCT/US03/25622 filed Aug. 15, 2003 International Search Report dated Mar. 10, 2004.

PCT/US2009/054955 filed Aug. 25, 2009 International Search Report and Written Opinion dated May 17, 2010.

PCT/US2010/044016 filed Jul. 30, 2010 International Preliminary Report on Patentability dated Feb. 5, 2013.

PCT/US2010/044016 filed Jul. 30, 2010 International Search Report and Written Opinion dated Sep. 24, 2010.

U.S. Appl. No. 11/837,472, filed Aug. 10, 2007, Non-Final Office Action dated Oct. 2, 2015.

U.S. Appl. No. 11/837,472, filed Aug. 10, 2007, Final Office Action dated Jun. 11, 2015.

U.S. Appl. No. 13/813,102, filed Sep. 10, 2013 Non-Final Office Action dated Apr. 22, 2016.

International Search Report and Written Opinion for PCT Application No. PCT/US2009/057566, dated Nov. 16, 2009.

CA 2,737,640 filed Sep. 18, 2012 Office Action dated Jul. 25, 2016.

U.S. Appl. No. 11/837,472, filed Aug. 10, 2007, Final Office Action dated May 10, 2016.

U.S. Appl. No. 13/813,102, filed Sep. 10, 2013 Advisory Action dated Nov. 22, 2016.

U.S. Appl. No. 13/813,102, filed Sep. 10, 2013 Final Office Action dated Sep. 27, 2016.

* cited by examiner

US 10,589,067 B2

MEDICAL DEVICE SECUREMENT SYSTEM

RELATED APPLICATION

This application is a continuation of co-pending U.S. application Ser. No. 12/666,272, now U.S. Pat. No. 8,734,400, filed Aug. 2, 2011, and entitled "MEDICAL DEVICE SECUREMENT SYSTEM," which is a U.S. National Phase under 35 U.S.C. § 371 of International Application No. PCT/US2009/057566, filed Sep. 18, 2009, and entitled "MEDICAL DEVICE SECUREMENT SYSTEM," which claims the benefit of U.S. Provisional Patent Application No. 61/098,704, filed Sep. 19, 2008, each of which is hereby expressly incorporated by reference in its entirety into this application.

BACKGROUND OF THE INVENTION

Field of the Invention

This invention relates to a securement system used to attach a catheter or other medical article to a patient.

Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

One aspect of the present invention is a securement system for securing a medical article to the skin of a patient. The system comprises a medical article having a connector fitting and a catheter hub and two anchor pads. Each anchor pad is spaced apart from the other and has a lower surface at least partially covered by an adhesive for contacting the patient's skin. The system further includes a retainer that has a body member. The body member has a channel formed therethrough about a channel axis, the channel being configured to retain at least a first portion of the medical article and having a first longitudinal access opening disposed on an underside of the body member to allow at least ingress of the first portion of the medical article into the channel. The retainer further includes two support members. Each support member is attached to one of the anchor pads and configured to support the body member. Each support member is spaced apart from the channel axis so as not to obstruct at least ingress of the first portion of the medical article into the channel. The retainer further includes a first abutment surface extending generally normal to the channel axis and configured to inhibit longitudinal movement of the medical article in a first longitudinal direction. The system further includes a clamp that has a collar configured to at least partially surround at least a second portion of the medical article. The collar has a second longitudinal access opening disposed on an underside of the collar to allow at least ingress of the second portion of the medical article into the collar. The second longitudinal access opening is aligned with the first longitudinal access opening. The clamp includes a second abutment surface extending generally normal to the channel axis and configured to inhibit longitudinal movement of the medical article in a second longitudinal direction opposite the first longitudinal direction. The system further includes interengaging structure configured to couple the clamp and the retainer and to allow movement of the clamp relative to the retainer in at least the first longitudinal direction, wherein movement of the clamp relative to the retainer in the first longitudinal direction moves the second abutment surface closer to the first abutment surface.

Another aspect of the present invention is a device for securing a medical article to a patient. The device includes two anchor pads. Each anchor pad is spaced apart from the other and has a lower surface at least partially covered by an adhesive for contacting the patient's skin. The device further includes a retainer that has a body member. The body member includes a channel formed therethrough about a channel axis. The channel is configured to retain at least a first portion of the medical article and has a first longitudinal access opening disposed on an underside of the body member to allow at least ingress of the first portion of the medical article into the channel. The device further includes two support members. Each support member is attached to one of the anchor pads and configured to support the body member. Each support member being spaced apart from the channel axis so as not to obstruct at least ingress of the first portion of the medical article into the channel. The device further includes a first abutment surface extending generally normal to the channel axis. The first abutment surface is configured to abut a corresponding first surface of the medical article and inhibit longitudinal movement of the medical article in a first longitudinal direction. The device further includes a clamp having a collar. The collar is configured to at least partially surround at least a second portion of the medical article. The collar has a second longitudinal access opening disposed on an underside of the collar to allow at least ingress of the second portion of the medical article into the collar. The second longitudinal access opening being aligned with the first longitudinal access opening. The device further includes a second abutment surface extending generally normal to the channel axis, the second abutment surface configured to abut a corresponding second surface of the medical article and inhibit longitudinal movement of the medical article in a second longitudinal direction opposite the first longitudinal direction. The device further includes interengaging structure configured to couple the clamp and the retainer and to allow movement of the clamp relative to the retainer in at least the first longitudinal direction, wherein movement of the clamp relative to the retainer in the first longitudinal direction moves the second abutment surface closer to the first abutment surface.

Another aspect of the invention is a device for securing a medical article to a patient. The device includes a retainer having a channel formed therethrough about a channel axis, the channel being configured to receive a first portion of the medical article and having a first longitudinal access opening disposed on an underside of the retainer. The device further includes two supports supporting the retainer. Each support is disposed on opposite sides of the channel axis so as to allow at least ingress of the first portion into the channel. The device further includes a clamp having a collar sized and shaped to at least partially surround a second portion of the medical article. The collar has a second longitudinal access opening disposed on an underside of the clamp to allow at least ingress of the second portion of the medical article into the collar. The second longitudinal access opening being generally aligned with the first longitudinal access opening. The device further includes interengaging structure coupling the clamp and the retainer so as to allow movement of the clamp relative to the retainer in a longitudinal direction and inhibit movement of the clamp relative to the retainer in a direction opposite to the longitudinal direction.

Another aspect of the invention is a method of securing a medical article to a patient, the medical article having a first distally-facing abutment surface and a first proximally-facing abutment surface. The method includes providing a securement device comprising a retainer, a clamp, and interengaging structure configured to couple the retainer to the clamp. Each of the retainer and clamp form a channel having a truncate cross-sectional shape. Each channel has an access opening dispose so as to face a patient's skin. The method further includes locating the securement device above the medical article so as to align portions of the medical article with the channels of the securement device, pressing the portions of the medical article through the access openings and into the channels so as to limit movement of the medical article in at least lateral and transverse directions relative to the securement device, and moving the clamp toward the retainer so as to limit movement of the medical article in a longitudinal direction relative to the securement device.

These and other features of the present invention will become readily apparent to those skilled in the art from the following detailed description of the preferred embodiments, which refers to the attached figures. The invention is not limited, however, to the particular embodiments that are disclosed.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features of the invention. The illustrated embodiments are shown in use with an illustrative example of a medical article that includes a catheter hub and extension set nut. For example, embodiments of the retainer may be used with Smiths Medical AdvantIV and ProtectIV catheters. However, the securement system may be used with other catheter designs. The illustration of the securement device in this context is not intended to limit the disclosed aspects and features of the invention to the specified embodiments or to usage only with the illustrated medical article. Those of skill in the art will recognize that the disclosed aspects and features of the invention are not limited to any particular embodiment of a securement system, and securement systems, which include one or more of the inventive aspects and features herein described, can be designed for use with a variety of medical articles (or combinations of medical articles) of varying design. One skilled in the art may also find additional applications for the devices and systems disclosed herein.

Figure 1:
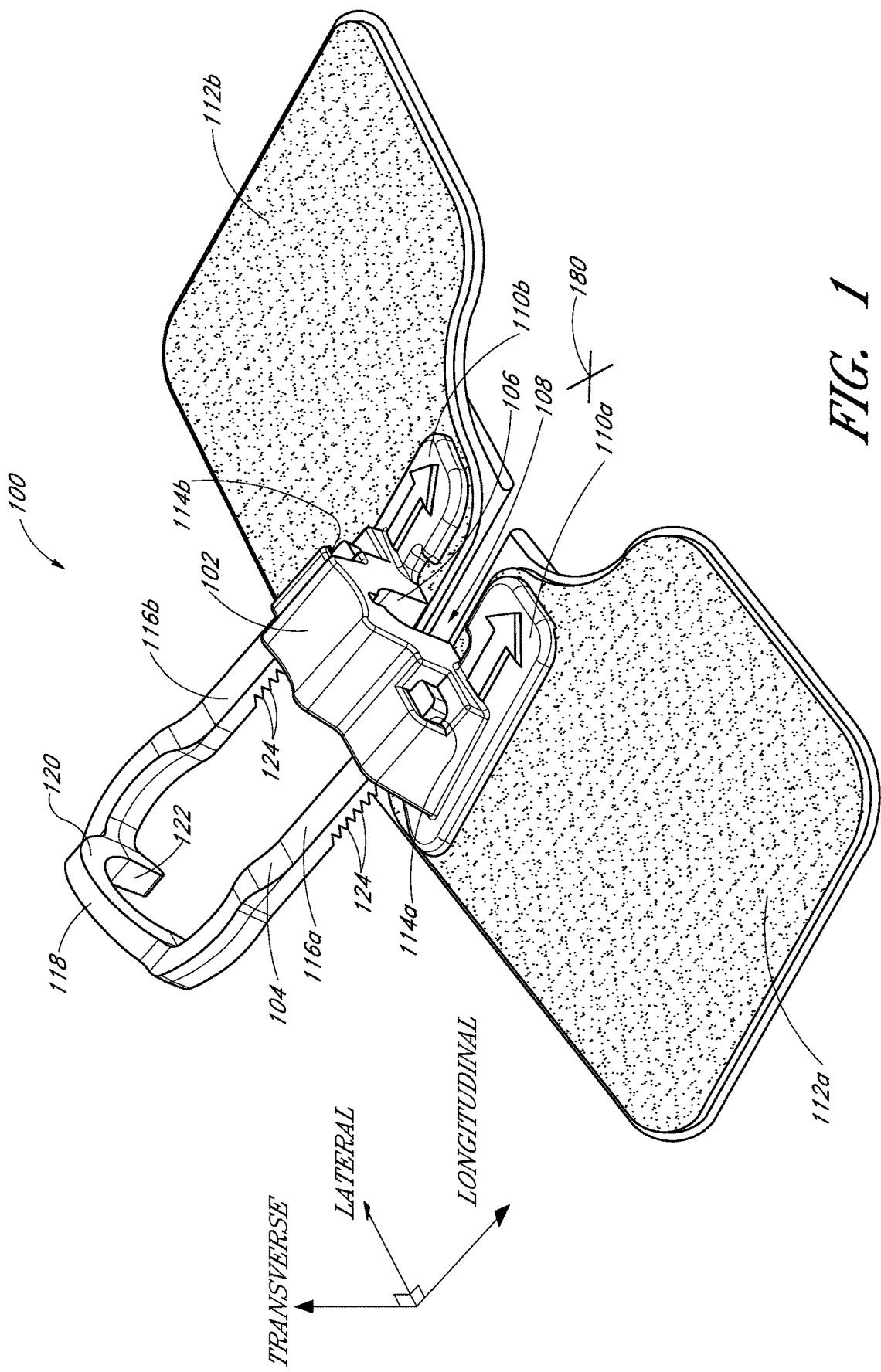
FIG. 1 is a perspective view of a securement system in accordance with a preferred embodiment of the present invention, illustrating a cooperating clamp and retainer supported by a pair of anchor pads.

To assist in the description of these components of the securement system, the following coordinate terms are used (see FIG. 1). A "longitudinal axis" is generally parallel to a portion of the medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present securement system, are used consistently with the description of the exemplary applications (i.e., the illustrative example of the use application). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described.

The securement system described herein is especially adapted to arrest transverse, lateral, and/or longitudinal movement of a medical article, such as a catheter, as well as to stabilize and hold the medical article against the patient. As described below, retention mechanisms to accomplish these goals include, among others, retention and/or abutment surfaces located on a retainer which receives the medical article, retention and/or abutment surfaces of a clamp which cooperates with the retainer and/or with the medical article itself, as well as a ratcheting mechanism by which the clamp may be tightened against the retainer. The ratchet mechanism allows a single securement system to be used with medical articles that have different longitudinal lengths. In some embodiments, the securement system is adapted to secure the medical article as close to the insertion site as possible, while also providing a low profile and maintaining a desired insertion angle, for example, 7 degrees between the needle and patient's skin. In some embodiments, the securement system is adapted to allow stable securement of a variety of medical articles of differing dimensions.

In some embodiments, a securement system generally includes two parts, a retainer and a clamp. The retainer includes a longitudinal channel configured to receive and secure at least a portion of a medical article. The longitudinal channel has a longitudinal access opening to allow ingress and egress of the medical article. The retainer also includes at least one support that is preferably disposed on the underside of the retainer at a position lower than the access opening. In some embodiments, the support includes left and right mounting wings that are integral with the body of the retainer and that are attached to left and right anchor pads. The lower surfaces of the left and right anchor pads attach to the patient's skin.

In some embodiments, the retainer includes one or more abutments, preferably an abutment surface, which cooperates with at least one contact point or surface on the medical article. The one or more abutments of the retainer extend generally normal to the longitudinal axis and can be, for example, but without limitation a surface, a wall of a slot, a ridge, a protuberance, a lip of a clip, or like structures. The abutment cooperates with the one or more contact points or surfaces of the medical article to inhibit longitudinal movement of the medical article through the retainer.

The securement system includes interengaging structure that secures the clamp to the retainer. For example, one of the clamp and retainer may include at least one arm that engages with corresponding structure of the other one of the clamp and retainer so as to secure the clamp relative to the retainer. When the clamp and the retainer are engaged, the arm can extend generally along a side of the channel of the retainer as is illustrated in FIG. 1. Of course more than one arm may be employed and or disposed so as to extend along the top or bottom of the channel between the clamp and the retainer.

In some embodiments, the clamp includes one or more abutments, preferably an abutment surface that cooperates with at least one contact point or surface on the medical article. The one or more abutments of the clamp extend generally normal to the longitudinal axis when the clamp is engaged with the retainer and can be, for example, but without limitation a surface, a wall of a slot, a ridge, a protuberance, a lip of a clip, or like structures. The one or more abutments of the clamp can face in a generally opposing direction to the retainer abutment, so as to cooperate with a contact point or surface on the medical article that faces in a generally opposing direction to the contact point or surface that cooperates with the retainer abutment. The clamp can be movable with respect to the retainer in at least a longitudinal direction, such that the abutments of the clamp and retainer can be moved closer together (or farther apart) to accommodate medical articles of varying dimensions.

The clamp and retainer can include corresponding interengaging structure so that their respective abutment surfaces can be securely tightened against the corresponding surfaces of medical articles of varying dimensions. The clamp and the retainer thus cooperate to inhibit at least longitudinal movement of the medical article through the retainer. In some embodiments, the clamp includes a collar having at least one abutment surface which extends generally parallel to the longitudinal axis when the clamp is engaged with the retainer. The abutment surface of the collar can have a flat or a curved shape, and can be configured to correspond to a surface of a portion of the medical article. The collar cooperates with the corresponding surface the medical article so as to limit transverse and/or lateral movement of the medical article at least when the clamp and retainer are tightened around the medical article. With this construction, the retainer can hold the retained portion of medical article in a secure and stable manner, close to the patient's skin, when the retained portion is positioned within the channel, while avoiding chafing or excoriating the skin.

With reference now to FIG. 1, a securement system 100 generally includes a retainer 102 and a clamp 104. The retainer 102 and clamp 104 include interengaging structure. The body of the retainer 102 includes a longitudinally-extending channel 106 which is configured to receive at least a portion of a medical article. The channel 106 can have a constant or variable cross section, such as a taper, along a portion or all of its length, and can be configured to roughly match the cross section of the portion of the medical article which it is adapted to retain.

The channel 106 is capable of receiving a portion or length of the medical article and is generally configured to house, to preferably grip, and to secure this portion of the medical article. In the illustrated embodiment an inner surface contour of the channel 106 preferably is selected depending on the geometry of the portion of the medical article to be retained. For example, in a retainer 102 that is configured to retain a portion of a medical article that has a constant outer diameter, the channel preferably has a constant radius along its length. In contrast, in a retainer 102 configured to retain a portion of a medical article that has a tapering outer surface, the channel preferably has a tapering inner surface and a radii that varies along the channel length. Additional embodiments of the channel 106 of the retainer can comprise a plurality of different radii and/or tapering regions. In this way, the size and shape of the channel 106 can be chosen to match or to approximate the size and shape of the medical article or portion thereof, e.g., the catheter hub, to be retained. By matching the inner surface contour of the channel 106 to the outer surface of the secured portion of a medical article, a more effective securement may be achieved. In addition or in the alternative, effective securement can also be achieved by the engagement of one or more abutment surfaces of the retainer 102 and clamp 104 with one or more contact surfaces on the medical article. for example, a proximally-facing surface 152 (i.e. first surface) and a distally-facing surface 154 (i.e. second surface) of the medical article. Each abutment surface can cooperate with a contact surface on the medical article to inhibit movement of the medical article relative to the retainer and/or clamp.

The channel 106 can extend through an arc of greater than 180°, so as to provide a degree of snap-fit between the retainer 102 and the medical article. The channel 106 has a longitudinal access opening 108 located on an underside of the retainer 102, to allow ingress or egress of the medical article. To facilitate placement of the medical article in the channel 106, the retainer 102 can include one or more features, such as a depression above the channel 106 and/or a groove disposed within the channel 106, which effectively thin a wall of the retainer 102 near the channel 106 to provide some degree of flexibility about the opening 108. The medical article can be installed or removed from the underside of the retainer via this access opening 108. Such an arrangement allows the medical provider to align at least a portion of the medical article with the retainer 102 prior to fixing the retainer to the patient's skin near an insertion site 180 (indicated by an "X" in FIG. 1).

The illustrated retainer 102 includes two supports 110(a), 110(b) disposed on a lower portion of the retainer 102. The supports 110(a), 110(b) can be disposed at a position lower than the access opening 108, so as to limit or prevent contact of the retained portion of the medical article with the skin of the patient. The supports 110(a), 110(b) are disposed on a pair of anchor pads 112(a), 112(b). The supports 110(a), 110(b) and the anchor pads 112(a), 112(b) are spaced apart so as to allow ingress and egress of the medical article therebetween. The anchor pads 112(a), 112(b) can have an adhesive disposed on their undersides so as allow attachment of the pads 112(a), 112(b) to the skin of a patient. In the illustrated embodiment, the arrows on the retainer 102 point in the direction toward the insertion site (i.e., in the proximal direction).

Each anchor pad 112(a), 112(b) desirably comprises a laminate structure with an upper plastic, paper or foam layer (e.g., closed-cell polyethylene foam) and a lower adhesive layer. The lower adhesive layer constitutes a lower surface of the anchor pad. The lower surface desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads can include suture holes in addition to the adhesive layer to further secure the anchor pad to the patient's skin.

In other variations, a hydrocolloid adhesive or zinc oxide-based adhesive can advantageously be used upon the anchor pads 112(a), 112(b) for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 112(a), 112(b) comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface of the anchor pad. The lower surface desirably is a medical-grade adhesive and can be either diaphoretic or nondiaphoretic, depending upon the particular application.

A surface of the upper foam layer constitutes an upper surface of the anchor pads 112(a), 112(b). The upper surface can be roughened by corona-treating the foam with a low electric charge. The roughened or porous upper surface can improve the quality of the adhesive joint (which is described below) between the supports 110(a), 110(b) and the anchor pads 112(a), 112(b). In a further variation, the flexible anchor pad can comprise an upper paper or other woven or nonwoven cloth or plastic layer in lieu of a roughened upper foam surface.

A removable paper or plastic release liner desirably covers the adhesive lower surface before use. The liner preferably resists tearing and desirably is divided into a plurality of pieces to ease attachment of the pad to a patient's skin. The liner comprises a folded over portion to define a pull tab. The pull tab can be utilized to remove the paper or plastic release liner from their adhesive lower surface before use. A medical provider uses the pull tab by grasping and pulling on it so that the liner is separated from the lower surface. The pull tab overcomes any requirement that the medical provider pick at a corner edge or other segment of the liner in order to separate the liner from the adhesive layer.

The pull tab of course can be designed in a variety of configurations. For example, the pull tab can be located along a center line of the anchor pad; or alternatively, the pull tab can be located along any line of the anchor pad in order to ease the application of the anchor pad onto the patient's skin at a specific site. For example, an area of a patient's skin with an abrupt bend, such as at a joint, can require that the pull tab be aligned toward one of the lateral ends of the anchor pad rather than along the center line.

The retainer 102 also includes one or more slots 114(a), 114(b) disposed on one or more sides of the channel 106. The illustrated embodiment includes two slots 114(a), 114(b). The slots 114(a), 114(b) are configured to receive and engage with at least portion of the clamp 104, as will be described in further detail below. In the illustrated embodiment, the slots 114(a), 114(b) extend in a longitudinal direction through the body of the retainer 102, and are angled slightly downward in the proximal direction relative to the patient's skin. In some embodiments, the slots extend only partway through the body of the retainer 102. Each slot 114(a), 114(b) has a length sufficient to support an arm 116(a), 116(b) of the clamp 104 and maintain the angle of the clamp 104 with respect to the retainer 102 (and thus, with respect to the skin of the patient) when the clamp 104 is engaged with the retainer 102.

The clamp 104 includes one or more arms 116(a), 116(b) configured for insertion into and engagement with the one or more slots 114(a), 114(b). The illustrated embodiment includes two arms 116(a), 116(b). The arms 116(a), 116(b) are connected at their distal ends by a collar 118. The collar 118 includes a proximally-facing surface 120 which abuts a corresponding, distally-facing surface of the medical article when it is received in the retainer 102 and the clamp 104 is tightened with the retainer 102. The collar 118 also includes a curved, inwardly-facing surface 122 which contacts an outer surface of the medical article when the medical article is secured in the system 100. The surface 122 can extend about the medical article through an arc of less than, about, or greater than 180° so as to inhibit lateral and/or transverse motion of the medical article to the extent desired. Each of the arms 116(a), 116(b) includes one or more ratchet teeth 124 which are configured to engage corresponding structure of the retainer 102, as will be described in further detail below.

Figure 2:
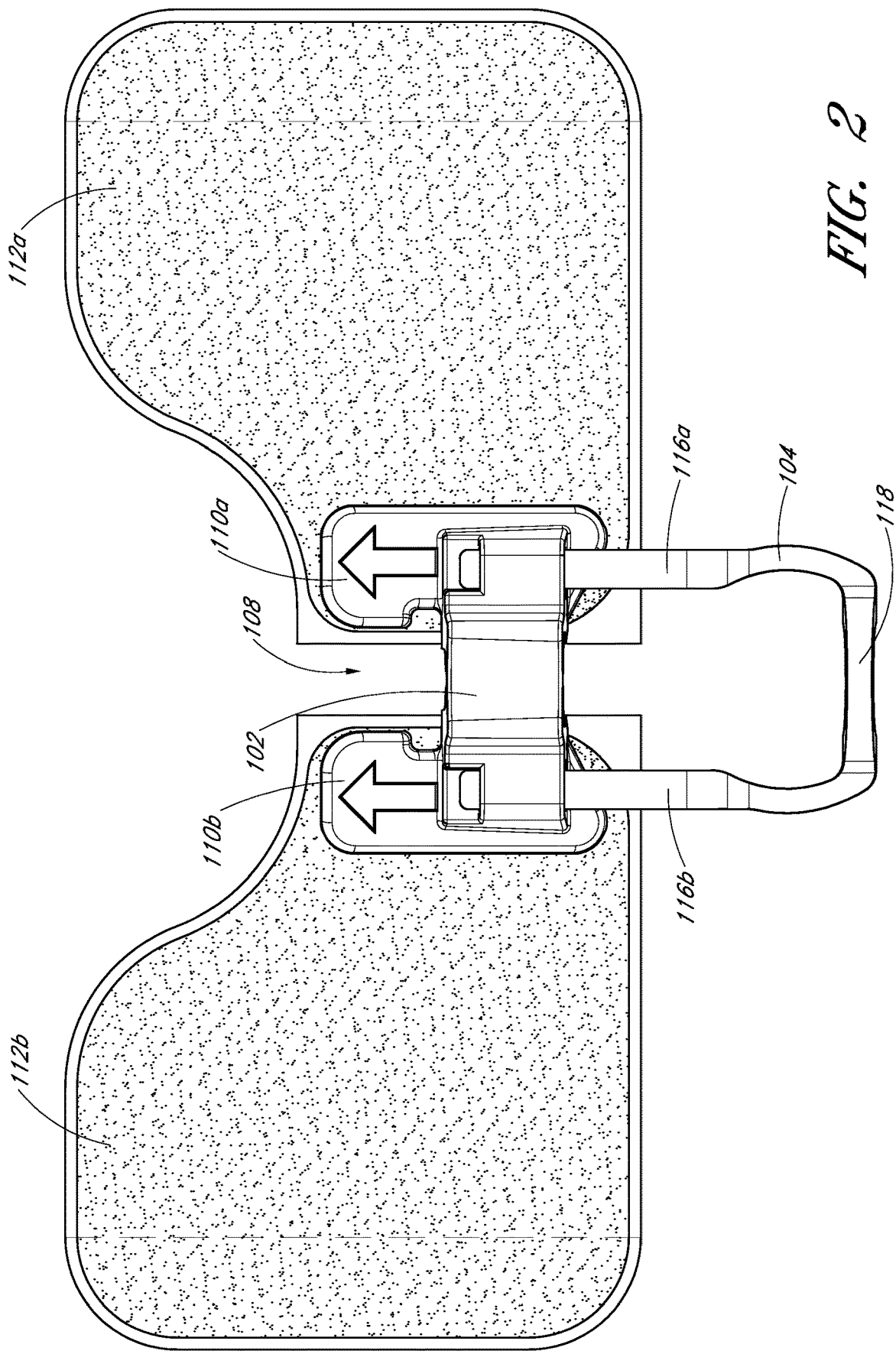
FIG. 2 is a top plan view of the securement system illustrated in FIG. 1.

FIG. 2 shows a plan view of the securement system 100. As can be seen in the figure, the arms 116(a), 116(b) extend from the collar 118 generally parallel to one another. In some embodiments, the arms can extend at an angle, toward each other or apart from each other, in a generally longitudinal direction.

Figure 3:
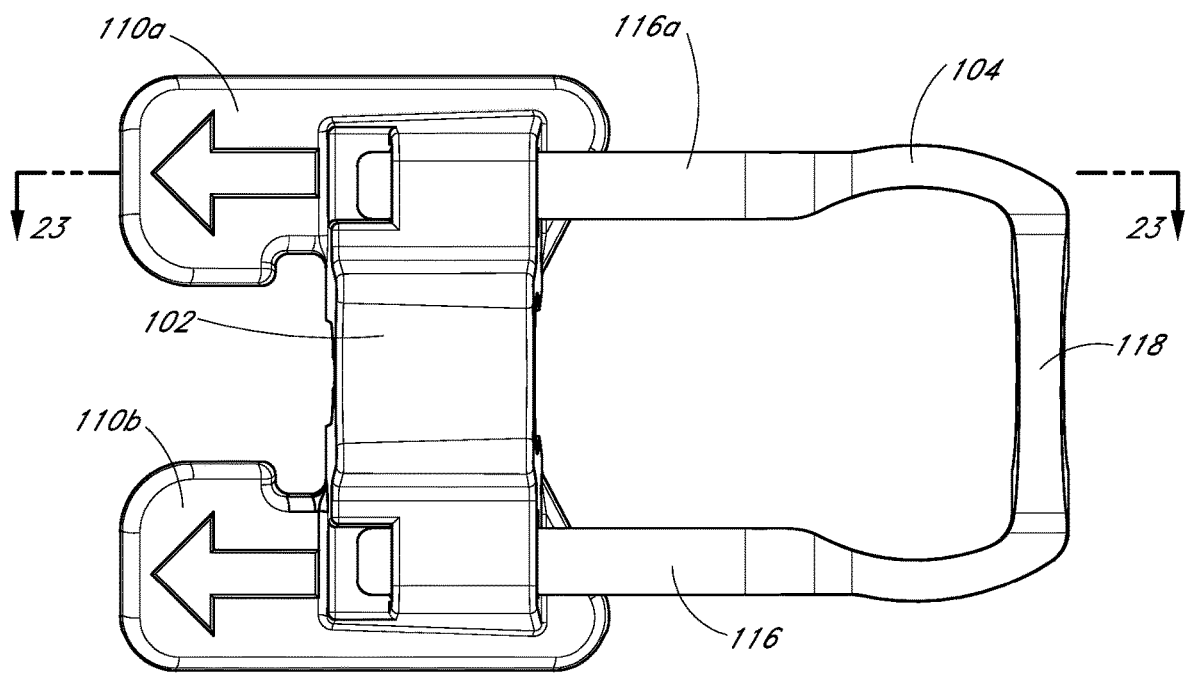
FIG. 3 is a top plan view of the clamp and retainer from FIG. 1 with arms of the clamp extending through corresponding slots in the retainer.
Figure 4:
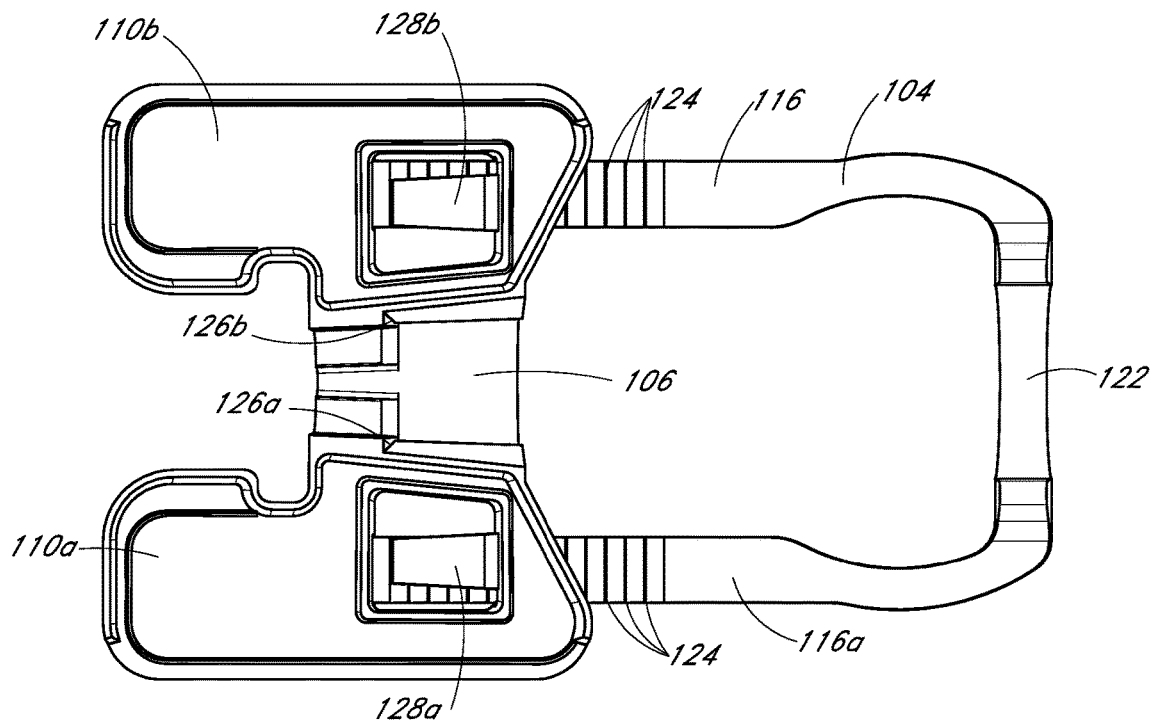
FIG. 4 is a bottom plan view of the clamp and retainer of FIG. 3 and shows a channel configured to receive a portion of a medical article.

FIGS. 3 and 4 are top and bottom plan views, respectively, of the clamp 104 and retainer 102 shown in FIG. 1. As can be seen in FIG. 4, the channel 106 of the retainer 102 includes a distally-facing abutment surface (i.e. first abutment surface) separated into two abutment surfaces 126(a), 126(b) by a narrow groove. At least one of the abutment surfaces 126(a), 126(b) is configured to abut a corresponding, proximally-facing surface of the medical article, e.g. proximally-facing surface 152 (FIG. 24), when the medical article is received in the channel 106 and when the clamp 104 is tightened with the retainer 102, so as to inhibit longitudinal movement of the medical article in at least a proximal direction.

As can also be seen in FIG. 4, the interengaging structure of the retainer 102 includes at last one beam 128(a), 128(b). The beam 128(a), 128(b) is disposed laterally of the channel 106, near the slots 114(a), 114(b). The illustrated beams 128(a), 128(b) are cantilevered beams that extend from a distal portion of the retainer 102 toward a proximal portion of the retainer 102. The beams 128(a), 128(b) can be configured to flex with respect to the portion of the retainer 102 to which they are attached, so as to facilitate engagement and/or disengagement of the clamp 104 with the retainer 102.

Figure 5:
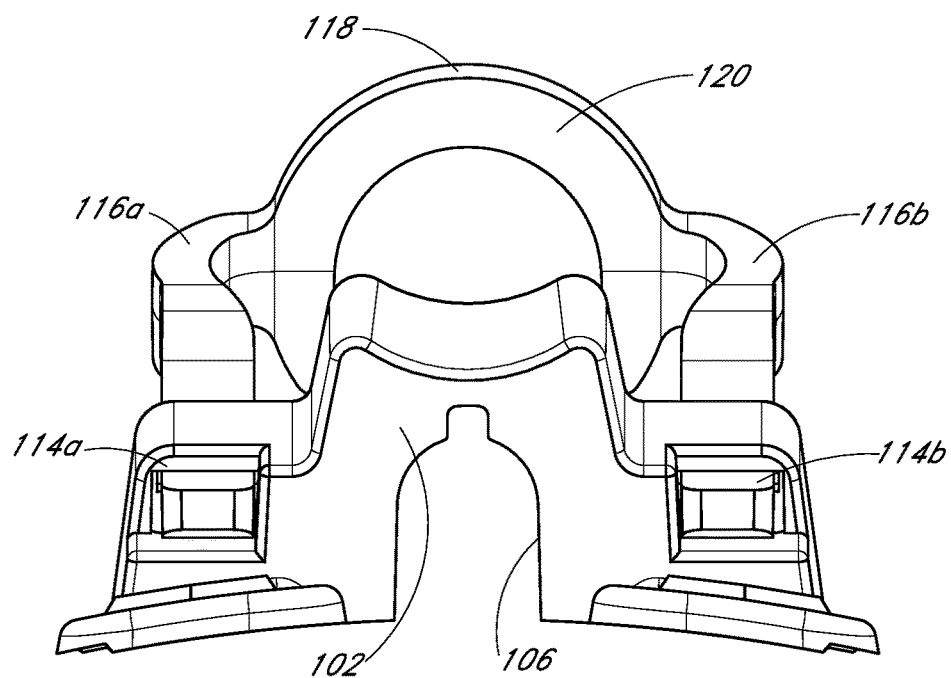
FIG. 5 is a front view of the clamp and retainer of FIG. 3.
Figure 6:
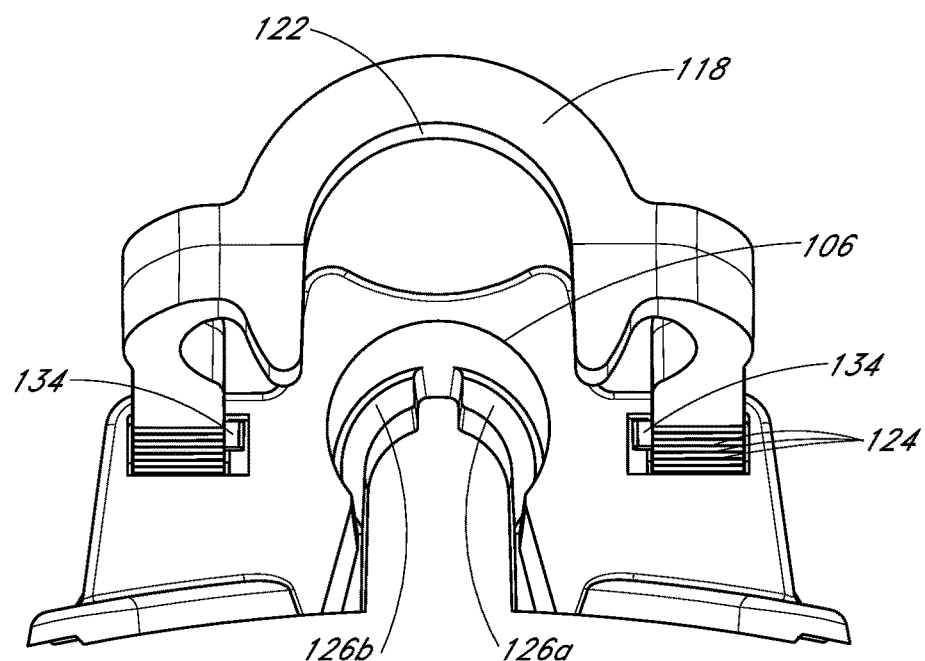
FIG. 6 is a rear view of the clamp and retainer of FIG. 3.
Figure 7:
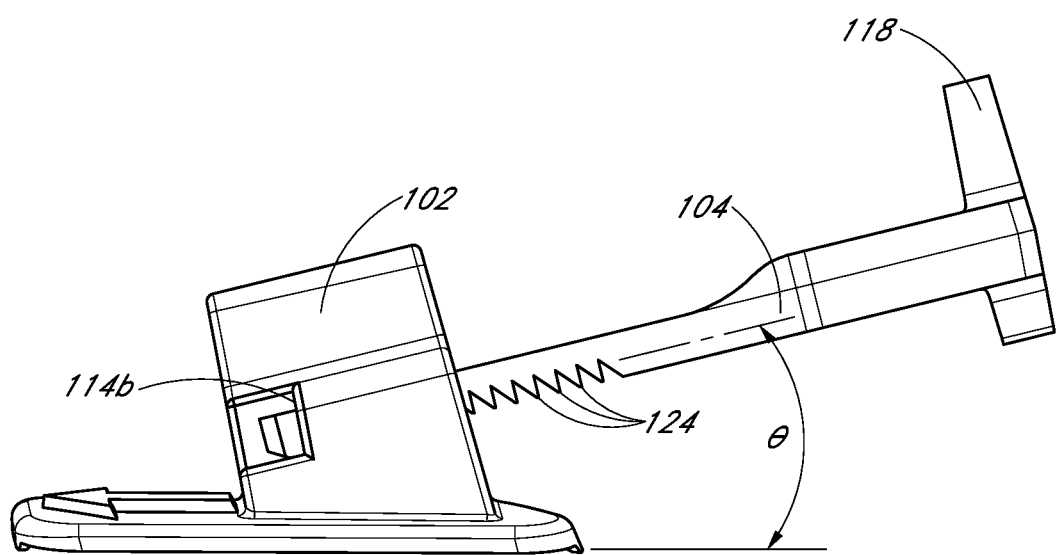
FIG. 7 is a side view of the clamp and retainer of FIG. 7.

FIGS. 5 through 7 show front, rear, and side views, respectively, of the clamp 104 and retainer 102 of FIG. 3. As most clearly shown in FIG. 7, an axis of the central channel 106 lies at an angle θ with respect to the base surfaces of the retainer 102. The desired angle θ between the medical article and the patient is created by angling the axis of the central channel 106. This angle is selected in order to align the axis of the channel 106 of the retainer with the desired incident angle with which the medical article is to contact the skin of the patient. A variety of different angles can be used, ranging from 0° to 45°, and more preferably from 5° to 25°. For instance, for the securement of intravenous catheters, it is desirable for the angle of incidence or θ of the catheter to the skin of the patient to be between about 7° to about 15°. For the securement of arterial catheters, it is desirable for the angle of incident of the catheter to the skin of the patient to be about 12.5°. By angling the axis of the channel 106 at the desired angle θ, which will depend upon the particular securement application (e.g., securing an arterial catheter, an intravenous catheter, etc.), the proper angle of incidence for a catheter can be maintained.

Figure 8:
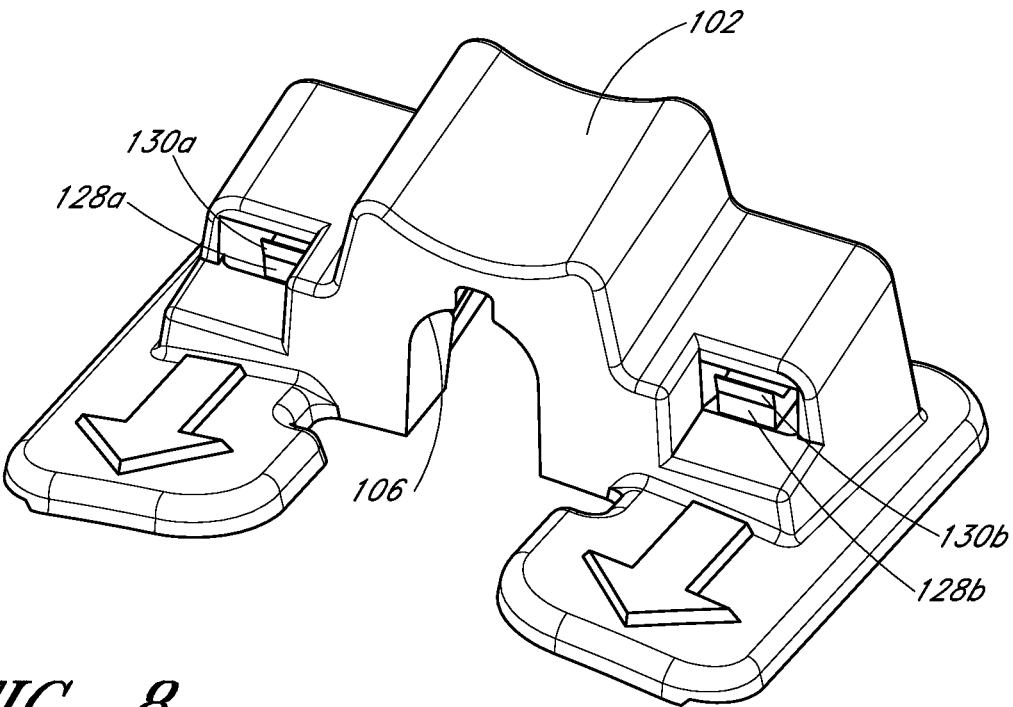
FIG. 8 is a front perspective view of the retainer from FIG. 3 without the clamp.
Figure 9:
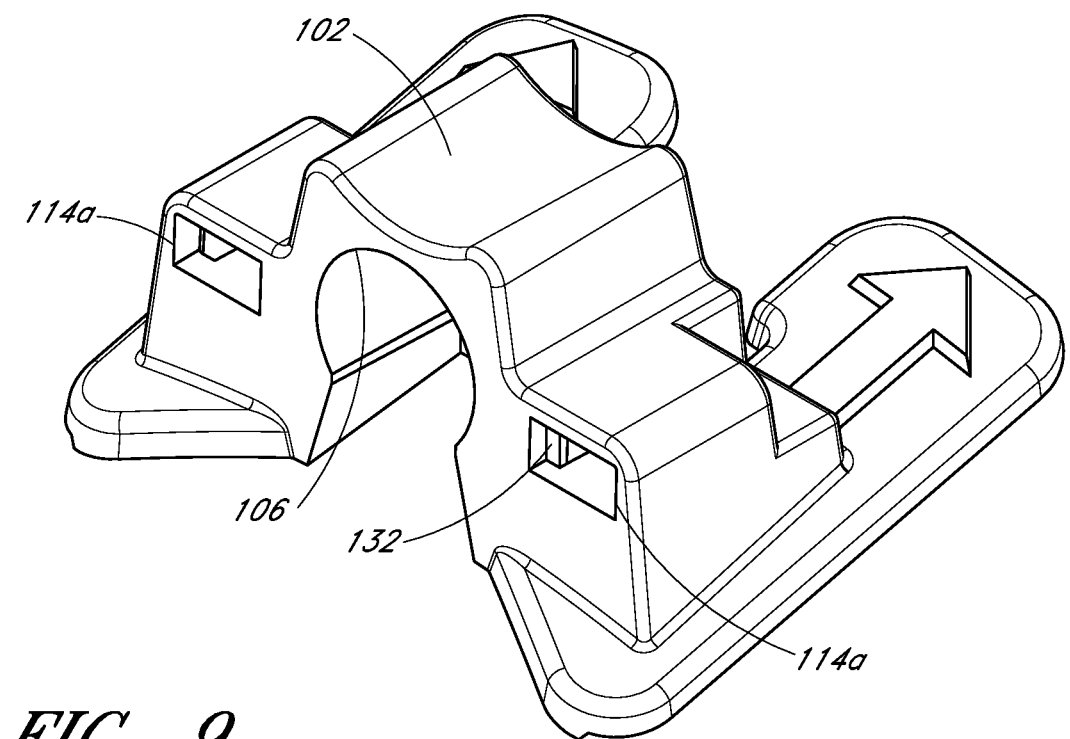
FIG. 9 is a rear perspective view of the retainer of FIG. 8.

FIGS. 8 and 9 show front and rear perspective views, respectively, of the retainer 102 of FIG. 3. As can be seen in FIG. 8, each beam 128(a), 128(b) includes one or more locking teeth 130(a), 130(b). When the arms 116(a), 116(b) of the clamp 104 are inserted into the corresponding slots 114(a), 114(b) of the retainer 102, the ratchet teeth 124 and the locking teeth 130(a), 130(b) cooperate inside the slots 114(a), 114(b) to adjustably secure the longitudinal position of the clamp 104 with respect to the retainer 102.

As can be seen in FIG. 9, the retainer 102 can also include one or more stops 132 disposed in or near the slots 114(a), 114(b). The stops 132 can be configured to cooperate with one or more protrusions 134 on the arms 116(a), 116(b) to inhibit longitudinal proximal movement of the clamp beyond a selected position during fabrication assembly and shipping. Of course the stops 132 and the protrusions 134 are not necessary to engage the clamp 104 with the retainer 102.

Figure 10:
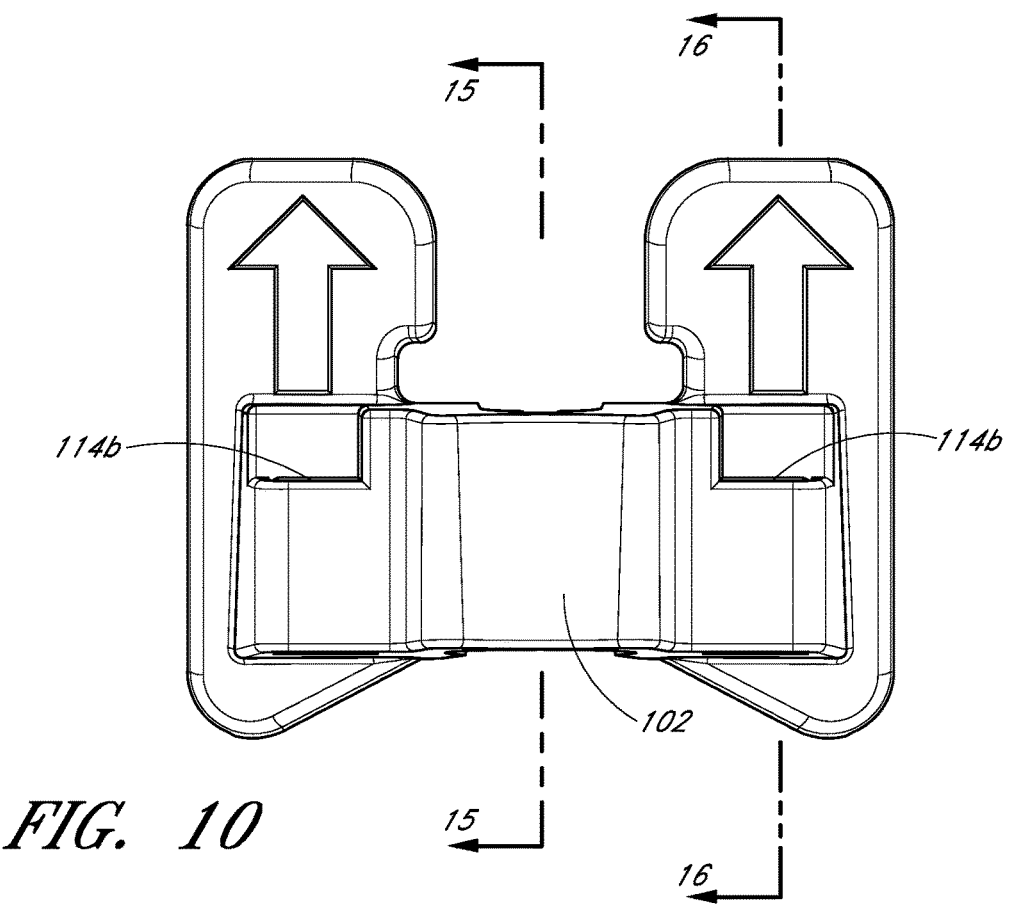
FIG. 10 is a top plan view of the retainer of FIG. 8.
Figure 11:
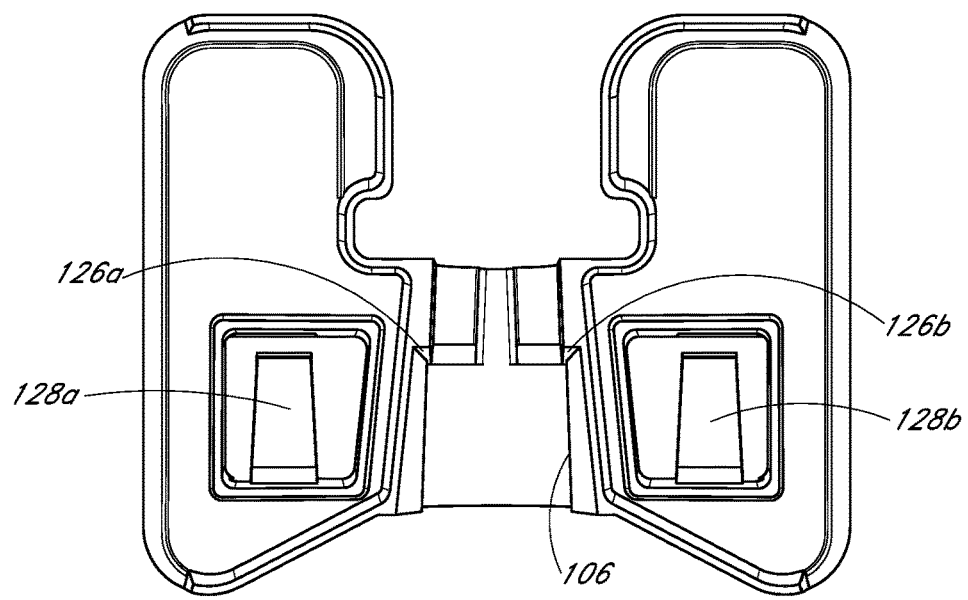
FIG. 11 is a bottom plan view of the retainer of FIG. 8.
Figure 12:
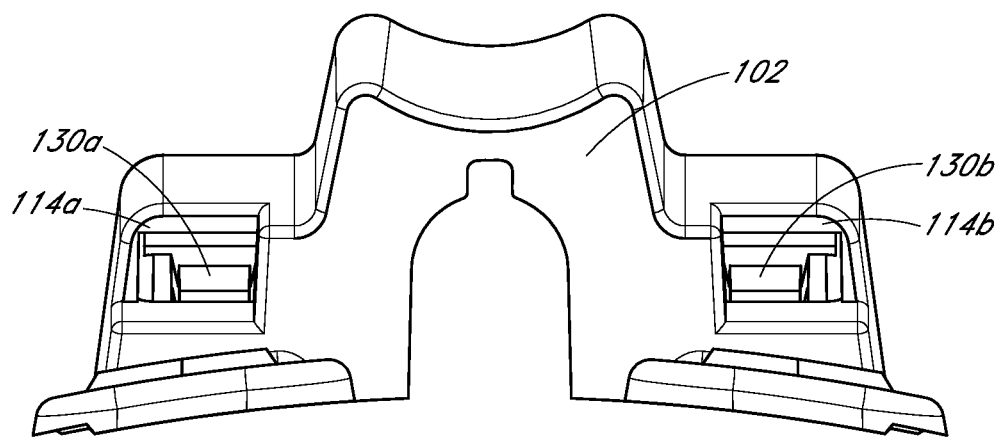
FIG. 12 is a front view of the retainer of FIG. 8.
Figure 13:
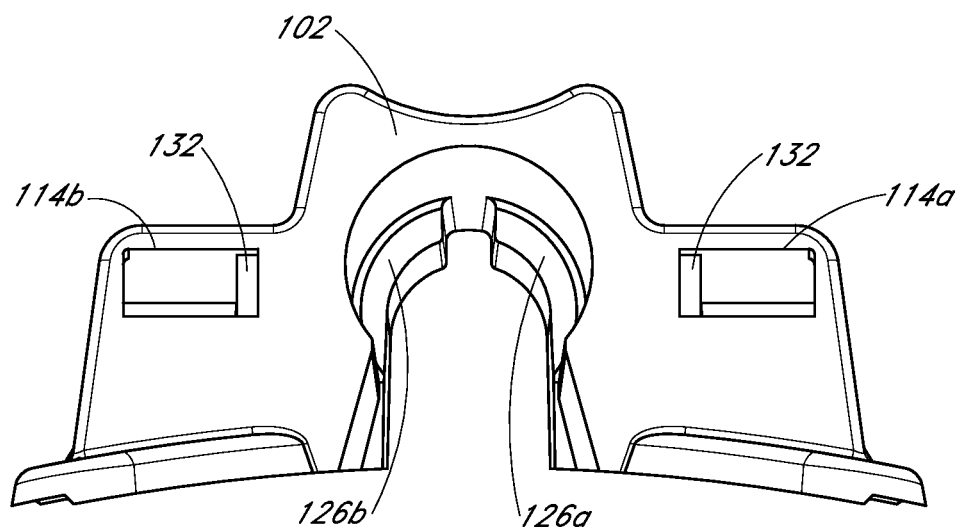
FIG. 13 is a rear view of the retainer of FIG. 8.
Figure 14:
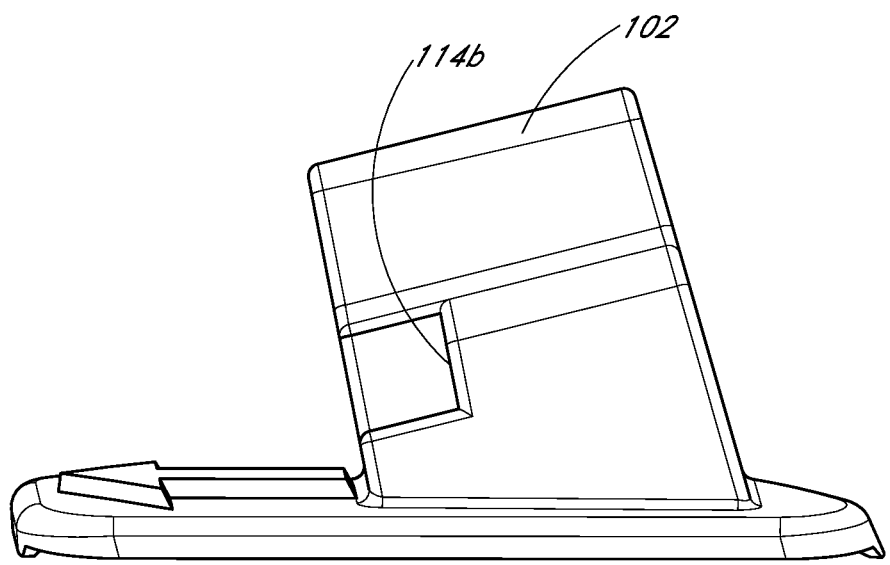
FIG. 14 is a side view of the retainer of FIG. 8.

FIGS. 10 and 11 show top and bottom plan views, respectively, of the retainer 102 of FIG. 8. FIGS. 12 through 14 show front, rear, and side views, respectively, of the retainer 102 of FIG. 8.

Figure 15:
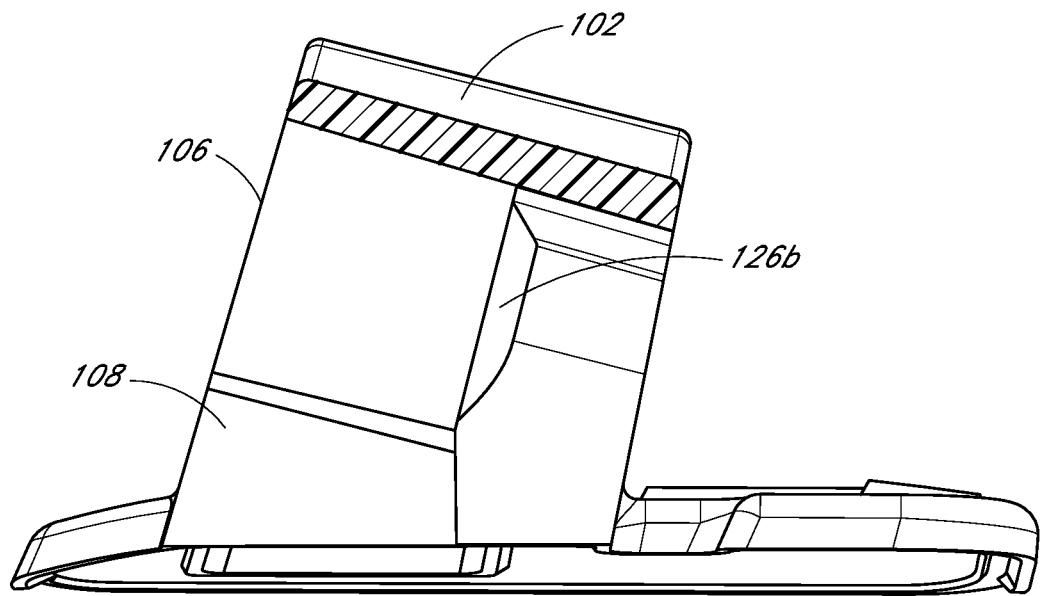
FIG. 15 is a cross-sectional view of the retainer taken through line 15-15 of FIG. 10 and shows an abutment surface configured to abut against a surface of a secured medical article.

FIG. 15 is a cross-sectional view of the retainer 102 taken through line 15-15 of FIG. 10 and shows an abutment surface 126(b) configured to abut against a surface of a secured medical article. Although the channel 106 can be formed in various shapes depending upon the desired application (e.g., depending upon a shape of the retained portion of the medical article for which the retainer is designed to be used), the channel 106 desirably has a sufficient length in the longitudinal direction to stabilize the connector fitting, catheter hub, or other medical article, rather than act as a fulcrum for the fitting. That is, the retainer 102 receives a sufficient length of the medical article to inhibit movement of the article in the lateral, longitudinal and transverse direction (i.e., to inhibit yaw, pitch and axial movement of the article).

Figure 16:
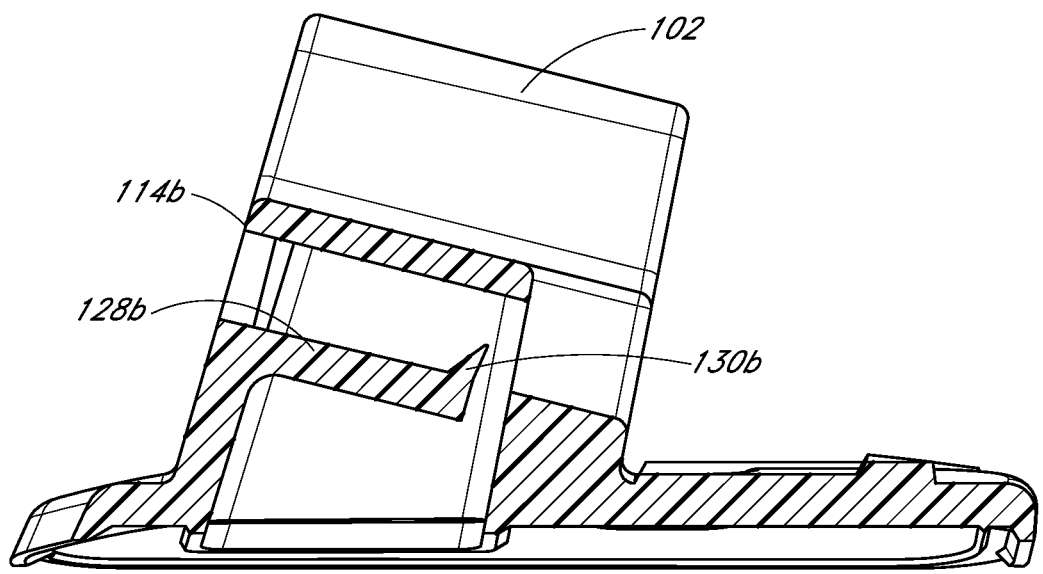
FIG. 16 is a cross-sectional view of the retainer taken through line 16-16 of FIG. 10 and shows a beam defining a surface of the slot and configured to engage with the arm of the clamp.

FIG. 16 is a cross-sectional view of the retainer taken through line 16-16 of FIG. 10 and shows the beam 128(b) defining a surface of the slot 114(b) and configured to engage with the arm 116(b) of the clamp 104.

Figure 17:
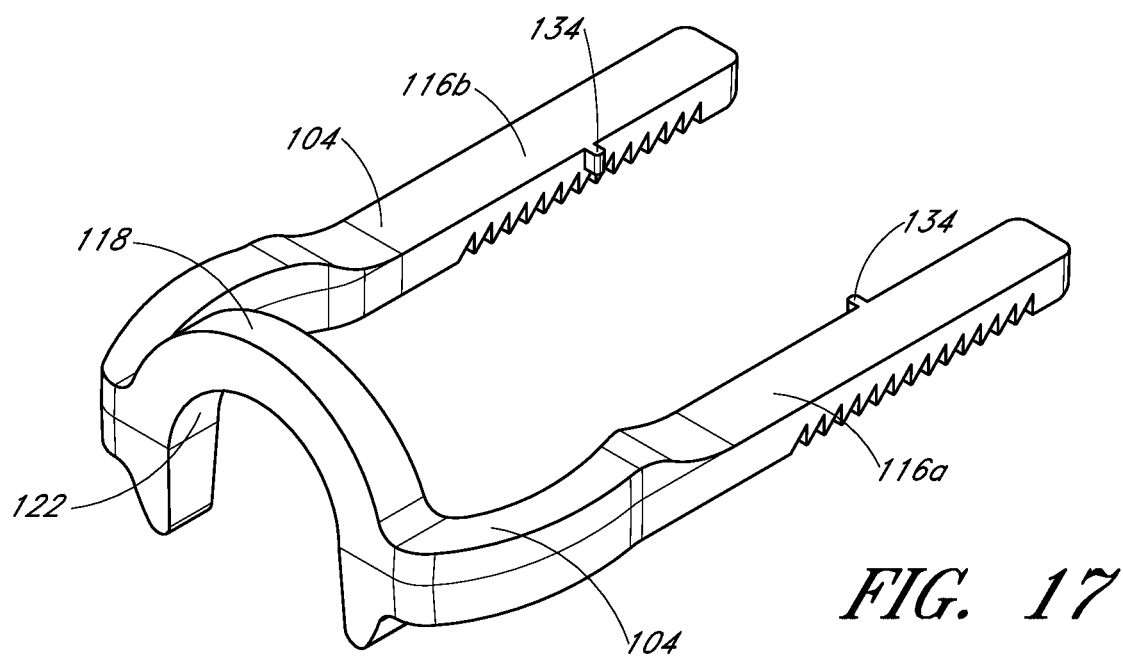
FIG. 17 is a top perspective view of the clamp from FIG. 3 removed from the retainer.
Figure 18:
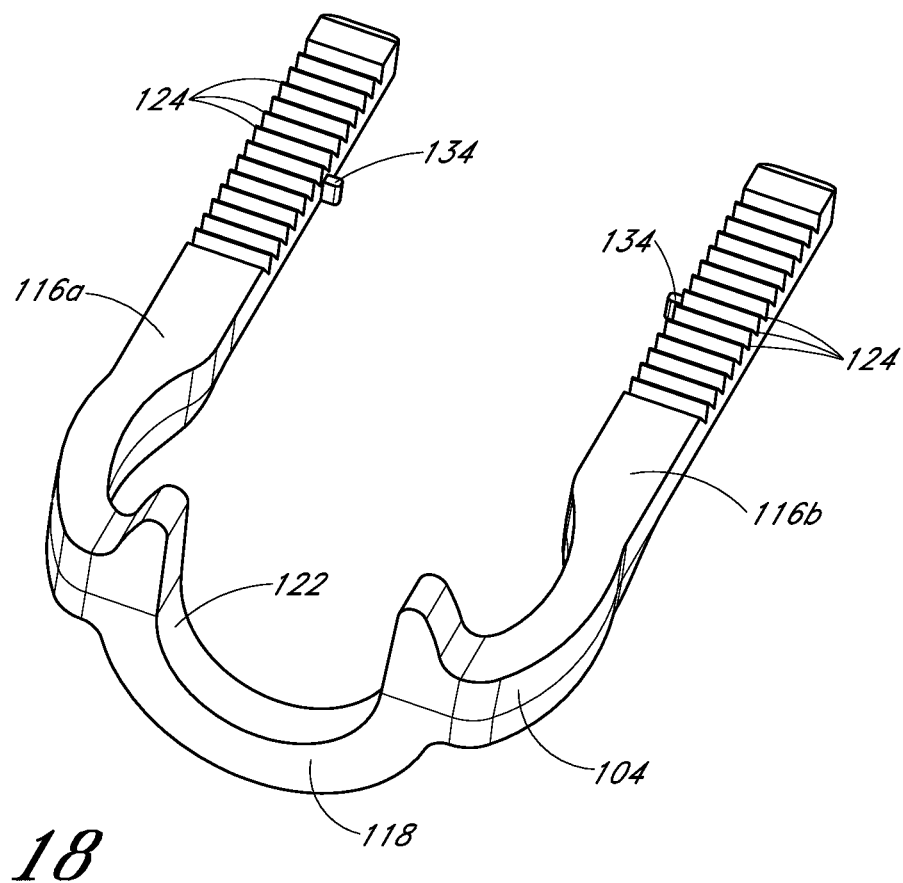
FIG. 18 is a bottom perspective view of the clamp of FIG. 17 and shows a series of teeth on each arm that engage with the beam illustrated in FIG. 16.

FIG. 17 is a top perspective view of the clamp 104 from FIG. 3 without the retainer 102. FIG. 18 is a bottom perspective view of the clamp 104 of FIG. 17 and shows a series of teeth 124 on each arm 116 that engage with the beam 128 illustrated in FIG. 16. As can be seen in the figures, the clamp 104 can include one or more protrusions 134. The protrusions 134 cooperate with the motion stops 132 of the retainer 102 to slightly inhibit longitudinal movement of the clamp 104 beyond a particular position when the clamp 104 is engaged with the retainer 102 during fabrication and assembly. For example, the protrusions 134 can be disposed on the arms 116(a), 116(b) of the clamp 104 such that, when the clamp 104 is inserted into the retainer 102 and the protrusions 134 abut the motion stops 132 during assembly, only a single ratchet tooth 124 passes over the locking tooth 130(a), 130(b) of each flex beam 128(a), 128(b). Such an arrangement may be beneficial during shipment by inhibiting the clamp 104 from closing against the retainer 102 while keeping the clamp 104 secured to the retainer 102.

With the application of some degree of force, however, the protrusions 134 (and thus, the clamp 104) can be moved past the motion stops 132 in order to close (or tighten) the clamp 104 in the direction of the retainer 102. During use, a medical provider simply pushes the clamp 104 in a proximal direction passing the protrusions 134 by the stops 132 until the medical article is secured between the opposing abutment surfaces on the clamp and retainer. By such a configuration, the protrusions 134 and the motion stops 132 cooperate to prevent self-closing of the system 100 during assembly and shipping but still allow the medical provider to secure a medical article during use.

Figure 19:
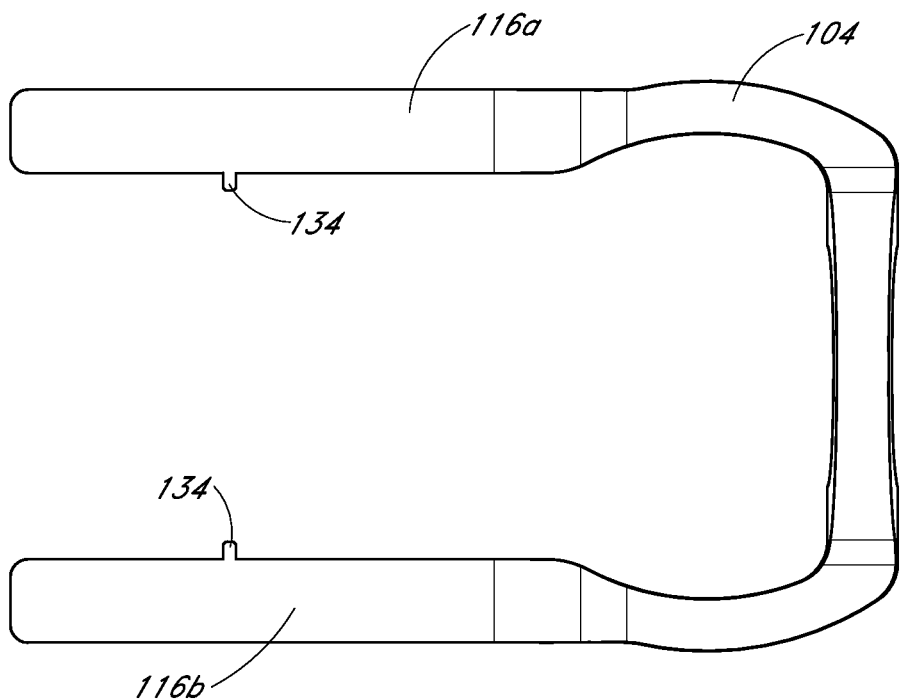
FIG. 19 is a top plan view of the clamp of FIG. 17 and shows an inwardly extending protrusion on each arm that cooperates with a stop in the slot of the retainer to inhibit longitudinal proximal movement of the clamp beyond a particular position during fabrication assembly and shipping.
Figure 20:
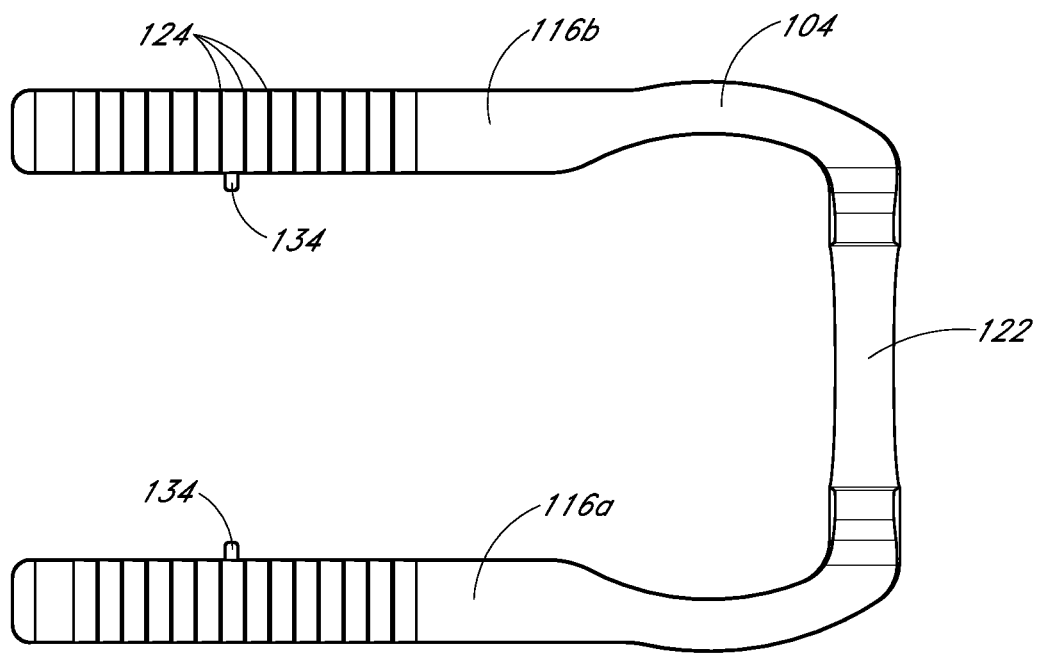
FIG. 20 is a bottom plan view of the clamp of FIG. 17.

FIG. 19 is a top plan view of the clamp of FIG. 17 and shows the inwardly extending protrusion 134 on each arm configured to cooperate with the stop 132 in the slot of the retainer to inhibit longitudinal proximal movement of the clamp beyond a particular position during fabrication assembly and shipping. FIG. 20 is a bottom plan view of the clamp of FIG. 17.

Figure 21:
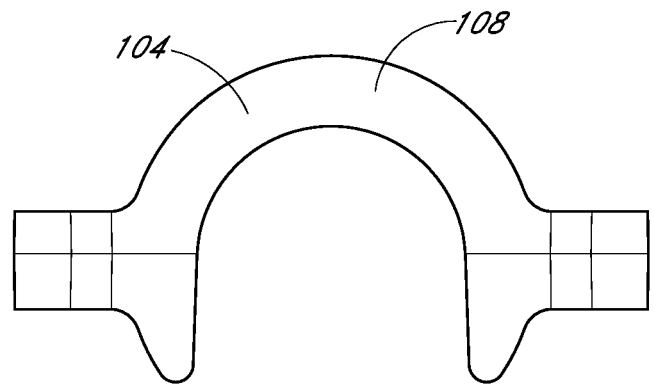
FIG. 21 is a rear view of the clamp of FIG. 17 and shows a collar disposed so as to abut a surface of a secured medical article.
Figure 22:
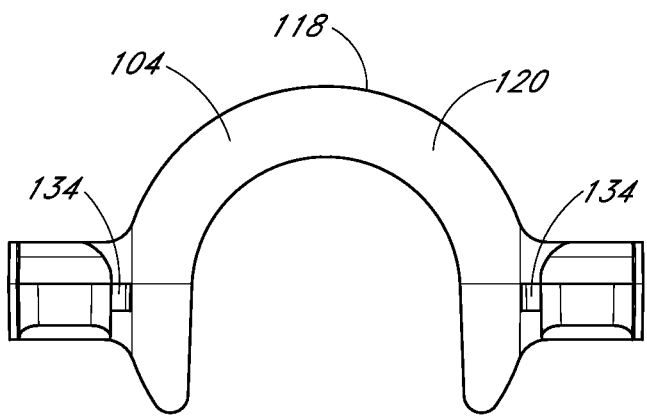
FIG. 22 is a front view of the clamp of FIG. 17.

FIG. 21 is a rear view of the clamp 104 of FIG. 17 and shows a collar disposed so as to abut a surface of a secured medical article. FIG. 22 is a front view of the clamp of FIG. 17.

Figure 23:
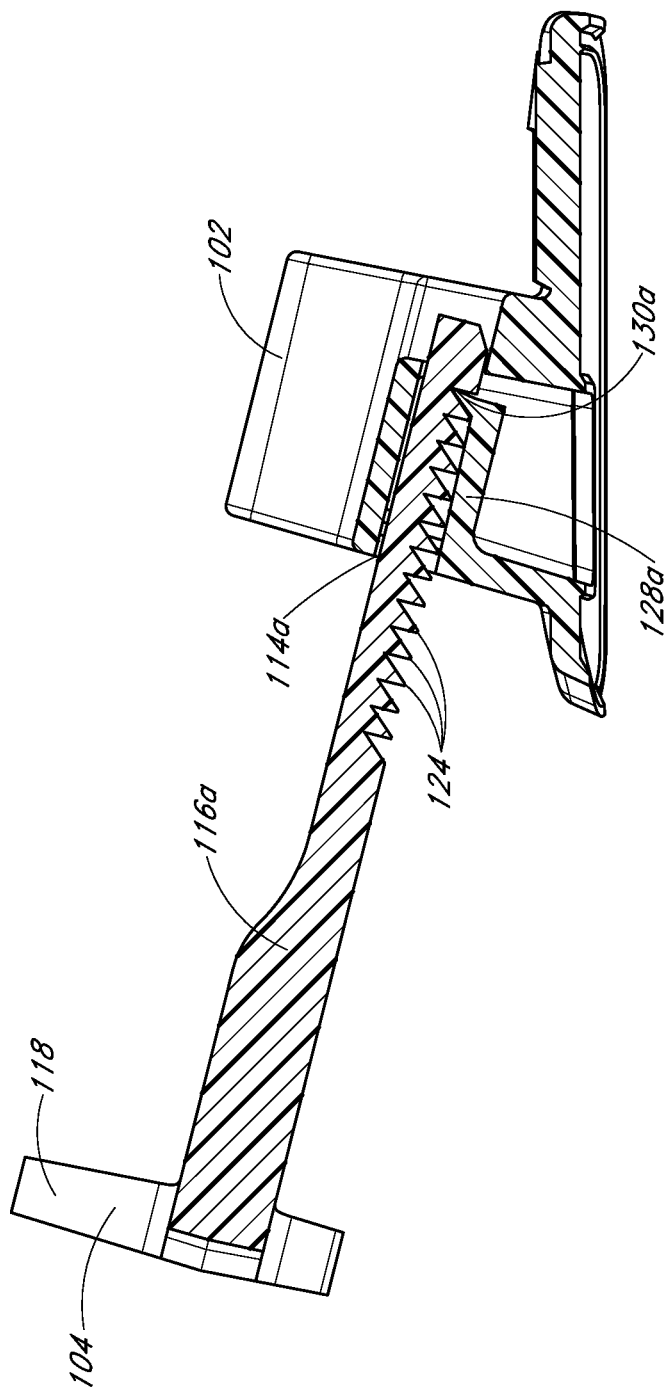
FIG. 23 is a cross-sectional view taken through line 23-23 of FIG. 3, illustrating the clamp engaged with the retainer with the clamp in a distal most position.

FIG. 23 is a cross-sectional view of the embodiment shown in FIG. 1, taken through line 23-23 of FIG. 3, and illustrates the engagement of the clamp 104 with the retainer 102. As the arms 116(a), 116(b) are inserted into the slots 114(a), 114(b), the leading edges of the arms 116(a), 116(b) abut the locking teeth 130(a), 130(b) of the retainer 104. With gentle force applied in the proximal direction, the arms 116(a), 116(b) can advance further into the slots 114(a), 114(b), as the cantilevered beams 128(a), 128(b) flex downward to allow successive engagement of the ratchet teeth 124. By such a configuration, the collar 118 can be moved closer to the retainer 102 and secured at any desired distance from the retainer.

The securement system 100 illustrated in FIGS. 1-23 is configured for single-use applications, and thus does not include a mechanism by which the clamp 104 may be easily released from the retainer 102 after the clamp 104 and retainer 102 have been tightened about a medical article. In some embodiments, however, a release mechanism can be included to allow for release and retraction of the clamp from the retainer. Such a mechanism can comprise, for example, one or more tangs which extend laterally from the flex beams to a point laterally beyond a portion of the retainer. To release the clamp in such an embodiment, the tangs can be depressed to disengage the locking tooth of the flex beam from the ratchet teeth of the clamp, allowing the clamp to be easily retracted (in a distal direction) from the slots and removed from the retainer if desired. In some such embodiments, the clamp can be provided with one or more stop members configured to prevent complete separation of the clamp from the retainer.

Further, although the embodiment illustrated includes ratchet teeth on the clamp arms and locking teeth on the retainer, alternative embodiments can of course include a reverse configuration in which ratchet teeth are provided on the retainer and one or more locking teeth are provided on an arm or arms of the clamp. Of course, the clamp and the retainer can include any other suitable corresponding structure that allows relative motion of the clamp and the retainer in a longitudinal direction, while providing securement of their relative positions as desired.

Although the embodiment illustrated includes arms extending from the clamp, alternative embodiments can of course include a reverse configuration in which the arms extend from the retainer and slide within slots in the clamp.

Figure 24:
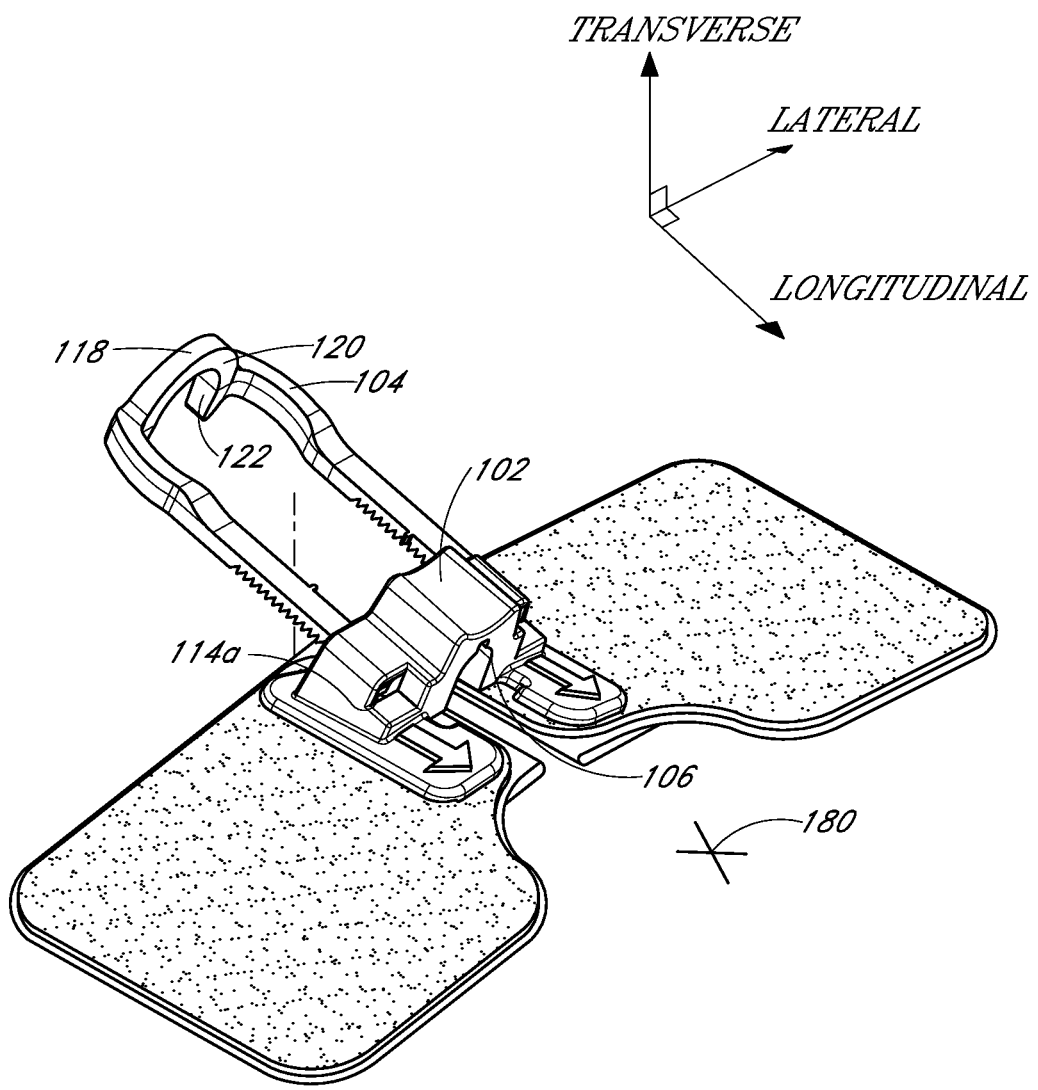
FIG. 24 is an exploded perspective view of the securement system shown in FIG. 1 prior to inserting an exemplary medical article into the clamp and retainer.
Figure 24:
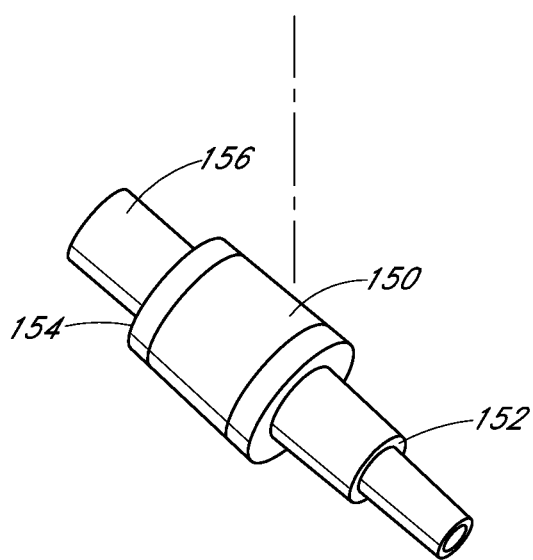

FIG. 24 is an exploded perspective view of the embodiment shown in FIG. 1, shown with an exemplary medical article 150 prior to being received in the retainer 102. The medical article has a proximally-facing surface 152, a distally-facing surface 154, and at least one outwardly-facing surface 156.

Figure 25:
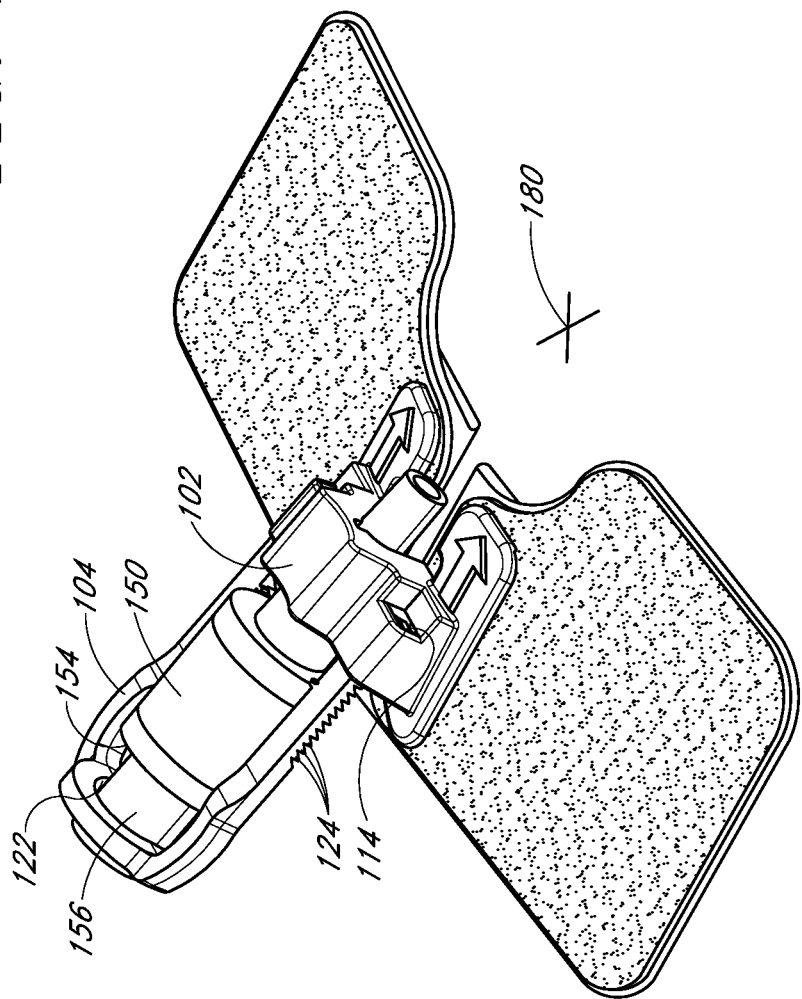
FIG. 25 is a view similar to FIG. 24 except that the medical article is received in both the retainer and clamp.

FIG. 25 shows the exemplary medical article 150 received in the channel 106 of the retainer 102, prior to insertion of the arms 116(a), 116(b) into the slots 114(a), 114(b). In this position, the abutment surfaces 126(a), 126(b) inside the channel 106 (see FIG. 4) cooperate with the proximally-facing surface 152 of the medical article 150 to inhibit longitudinal movement of the article 150 in a proximal direction beyond a desired position.

Figure 26:
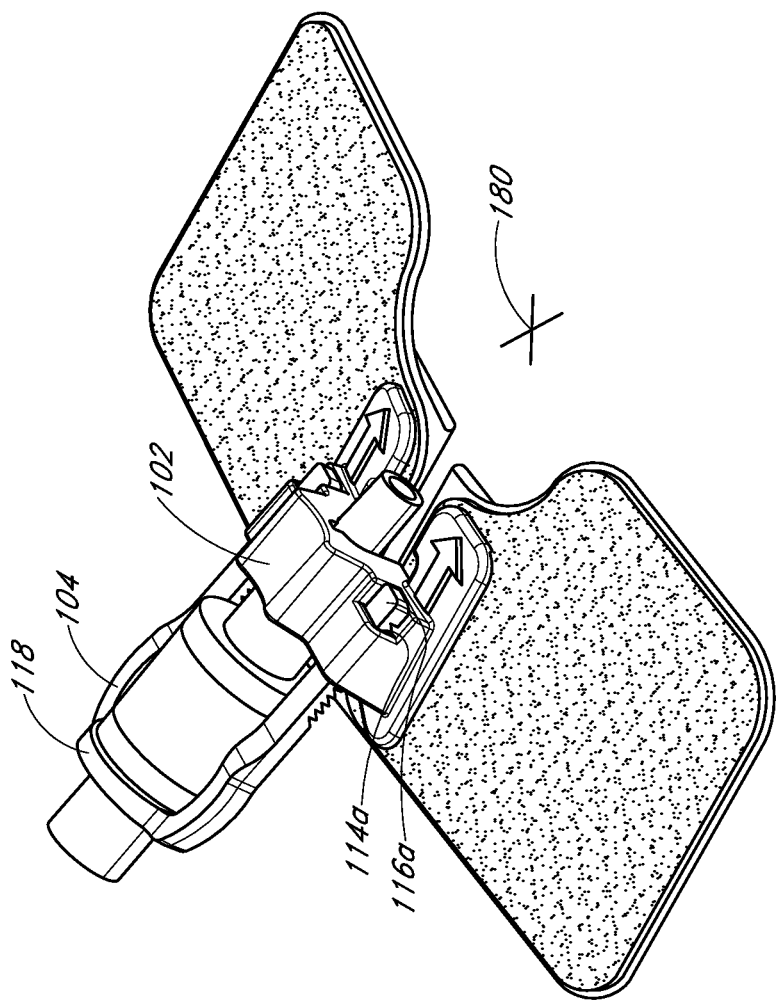
FIG. 26 is a view similar to FIG. 25 except that the clamp is advanced in a proximal direction toward the retainer to secure the medical article therebetween and inhibit movement of the medical article in both the proximal and distal directions.

FIG. 26 shows the clamp 104 engaged with the retainer 102, with the two parts tightened together about the medical article 150. In the illustrated secured position, the proximally-facing surface 120 (i.e. second abutment surface) of the clamp 104 cooperates with the distally facing surface 154 (i.e. second surface) of the medical article 150 to inhibit longitudinal movement of the article 150 in a distal direction beyond a desired position, and the inwardly-facing surface 122 of the collar 118 cooperates with the outer surface 156 of the medical article 150 to inhibit both lateral and transverse movement of the medical article 150.

Figure 27:
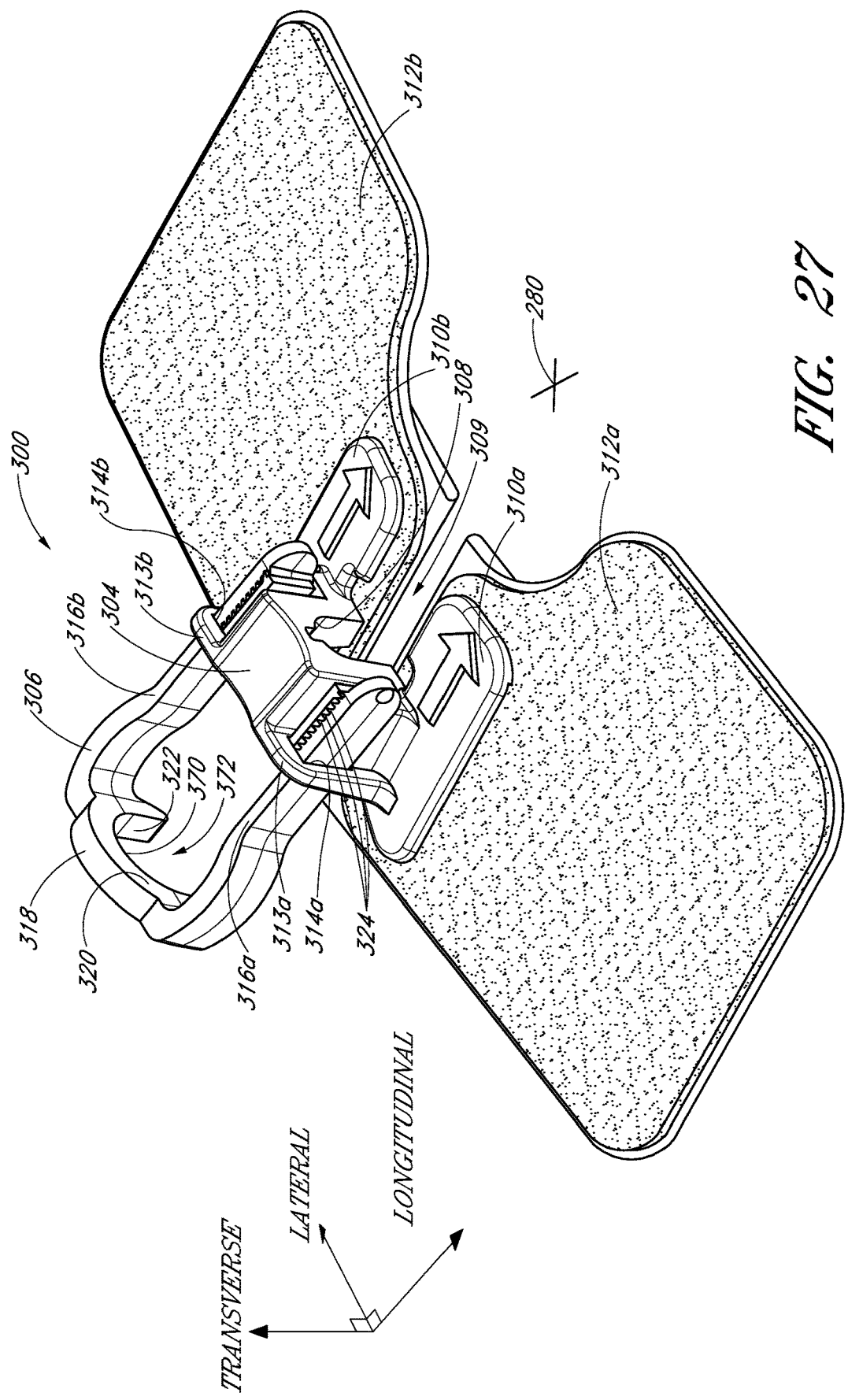
FIG. 27 is a perspective view of a securement system according to another preferred embodiment of the present invention, illustrating a cooperating clamp and retainer supported by a pair of anchor pads.

FIG. 27 is a perspective view of a securement system 300 according to another preferred embodiment of the present invention. The securement system 300 generally includes a retainer 304 and a clamp 306 which include interengaging structure. The body of the retainer 304 includes a longitudinally-extending channel 308 which is configured to receive at least a portion of a medical article. The channel 308 can have a constant or variable cross section, such as a taper, along a portion or all of its length, and can be configured to roughly match the cross section of the portion of the medical article which it is adapted to retain. The channel 308 can extend through an arc of greater than 180°, so as to provide a degree of snap-fit between the retainer 304 and the medical article. The channel 308 has a longitudinal access opening 309 located on an underside of the retainer 304, to allow ingress or egress of the medical article. To facilitate placement of the medical article in the channel 308, the retainer 304 can include one or more features, such as a depression above the channel 308 and/or a groove disposed within the channel 308, which effectively thin a wall of the retainer 304 near the channel 308 to provide some degree of flexibility about the opening 309. The medical article can be installed or removed from the underside of the retainer via this access opening 309. Such an arrangement allows the medical provider to align at least a portion of the medical article with the retainer 304 prior to fixing the retainer to the patient's skin near an insertion site 380 (indicated by the "X" in FIG. 27).

The illustrated retainer 304 includes two supports 310(a), 310(b) disposed on a lower portion of the retainer 304. The supports 310(a), 310(b) can be disposed at a position lower than the access opening 309, so as to limit or prevent contact of the retained portion of the medical article with the skin of the patient. The supports 310(a), 310(b) are disposed on a pair of anchor pads 312(a), 312(b). The supports 310(a), 310(b) and the anchor pads 312(a), 312(b) are spaced apart so as to allow ingress and egress of the medical article therebetween. The anchor pads 312(a), 312(b) can have an adhesive disposed on their undersides so as allow attachment of the pads 312(a), 312(b) to the skin of a patient. In the illustrated embodiment, the arrows on the retainer 304 point in the direction toward the insertion site (i.e., in the proximal direction).

The retainer 304 also includes wings 313(a), 313(b) that extend laterally from either side of the body of the retainer 304 to form two slots 314(a), 314(b), one on each side of the retainer 304. The slots 314(a), 314(b) are configured to receive and engage with at least portion of the clamp 306, as will be described in further detail below. In the illustrated embodiment, the wings 313(a), 313(b) extend in a longitudinal direction for only a portion of the longitudinal length of the retainer 304. The slots 314(a), 314(b) extend through the length of the wings 313(a), 313(b) and are angled slightly downward in the proximal direction. Each slot 314(a), 314(b) has a length sufficient to support an arm 316(a), 316(b) of the clamp 306 and maintain the angle of the clamp 306 with respect to the retainer 304 (and thus, with respect to the skin of the patient) when the clamp 306 is engaged with the retainer 304.

The clamp 306 includes two arms 316(a), 316(b), at least a portion of each arm being configured for insertion into the slots 314(a), 314(b) and engagement with a locking tooth 330(a), 330(b) on the retainer 304. The arms 316(a), 316(b) are connected at their distal ends by a collar 318. The collar can be configured to at least partially surround a distal portion of the medical article, either loosely or closely, to thereby form a receiving channel 370 for the distal portion of the medical article. In some embodiments, the collar can be configured to provide some degree of snap-fit with a distal portion of the medical article. The collar can be configured to extend through an arc of less than about 180°, up to about 180°, or more than 180°, depending on the application. The collar 118 has an access opening 372 at its underside which is sized at least large enough to receive a distal portion of the medical article into the receiving channel 370 of the collar.

The collar 318 includes a proximally-facing surface 320 which is configured to abut a corresponding, distally-facing surface of the medical article when it is received in the retainer 304 and the clamp 306 is tightened toward the retainer 304, so as to inhibit longitudinal movement of the medical article in at least a distal direction. The collar 318 also includes a curved, inwardly-facing surface 322 which is configured to contact a radially outwardly-facing surface of the medical article when the medical article is secured in the system 300. The surface 322 can extend about the medical article through an arc of less than, about, or greater than 180° so as to inhibit lateral and/or transverse motion of the medical article to the extent desired. Each of the arms 316(a), 316(b) includes one or more ratchet teeth 324 which are configured to engage corresponding structure of the retainer 304, as will be described in further detail below.

Figure 28:
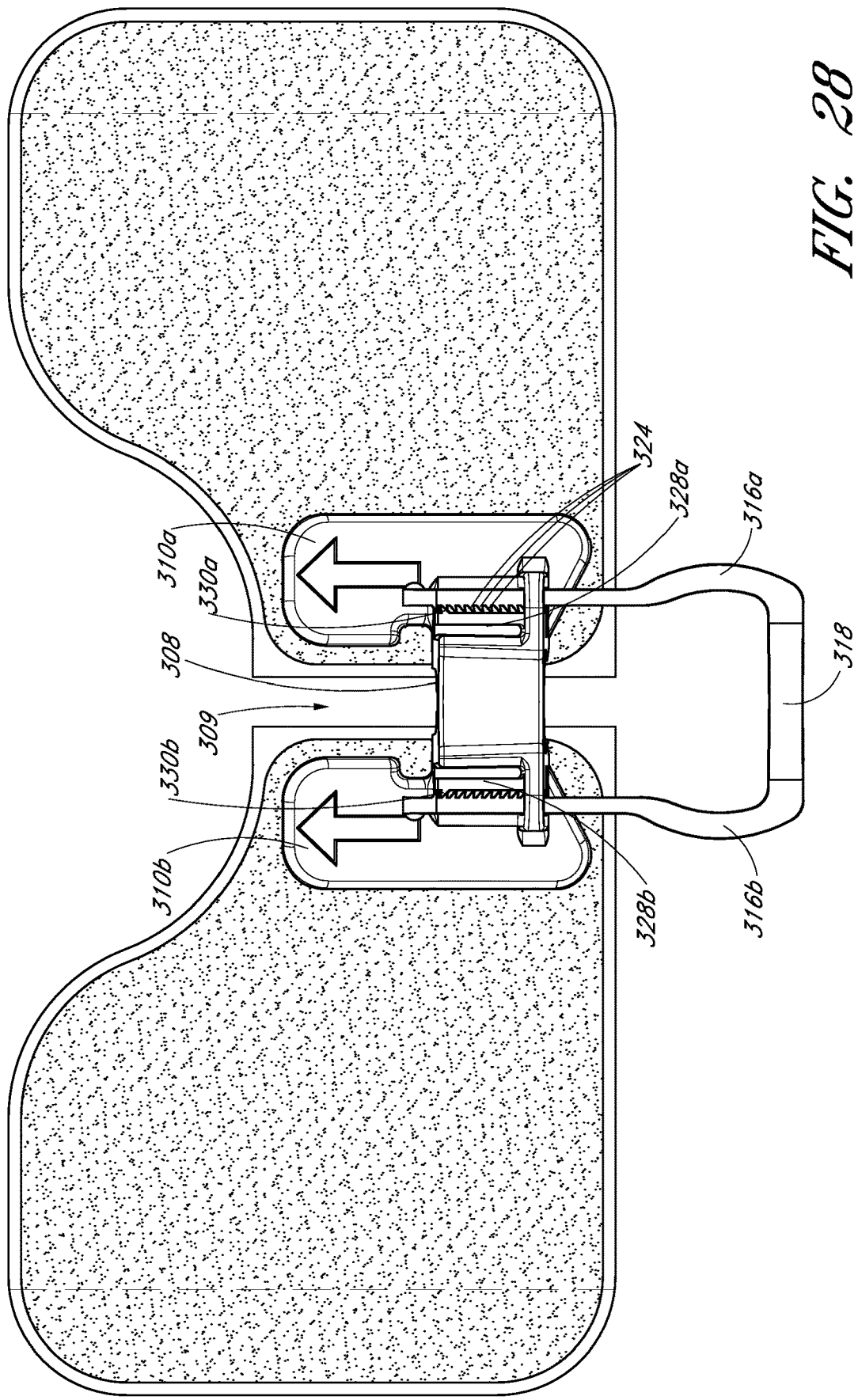
FIG. 28 is a top plan view of the securement system illustrated in FIG. 27.

As can be seen in FIG. 28, the retainer also includes two beams 328(a), 328(b). Each beam 128(a), 128(b) is disposed laterally of the channel 106, near the slots 314(a), 314(b). The illustrated beams 328(a), 328(b) are cantilevered beams that extend from a distal portion of the retainer 304 toward a proximal portion of the retainer 304. The beams 328(a), 328(b) can be configured to flex with respect to the portion of the retainer 304 to which they are attached, so as to facilitate engagement and/or disengagement of the clamp 306 with the retainer 304. Each beam 328(a), 328(b) includes one or more locking teeth 330(a), 330(b) at or near its proximal end. When the arms 316(a), 316(b) of the clamp 306 are inserted through the corresponding slots 314(a), 314(b) of the retainer 304, the ratchet teeth 324 and the locking teeth 330(a), 330(b) cooperate with the slots 314(a), 314(b) to adjustably secure the longitudinal position of the clamp 306 with respect to the retainer 304. The arms 316(s), 316(b) also cooperate with the slots 314(a), 314(b) to generally fix the angle of the clamp 306 with respect to the retainer 304 (see FIG. 33). In the illustrated embodiment, the arms 316(a), 316(b) extend from the collar 318 generally parallel to one another. In some embodiments, the arms extend at an angle, toward each other or apart from each other in a generally longitudinal direction.

Figure 29:
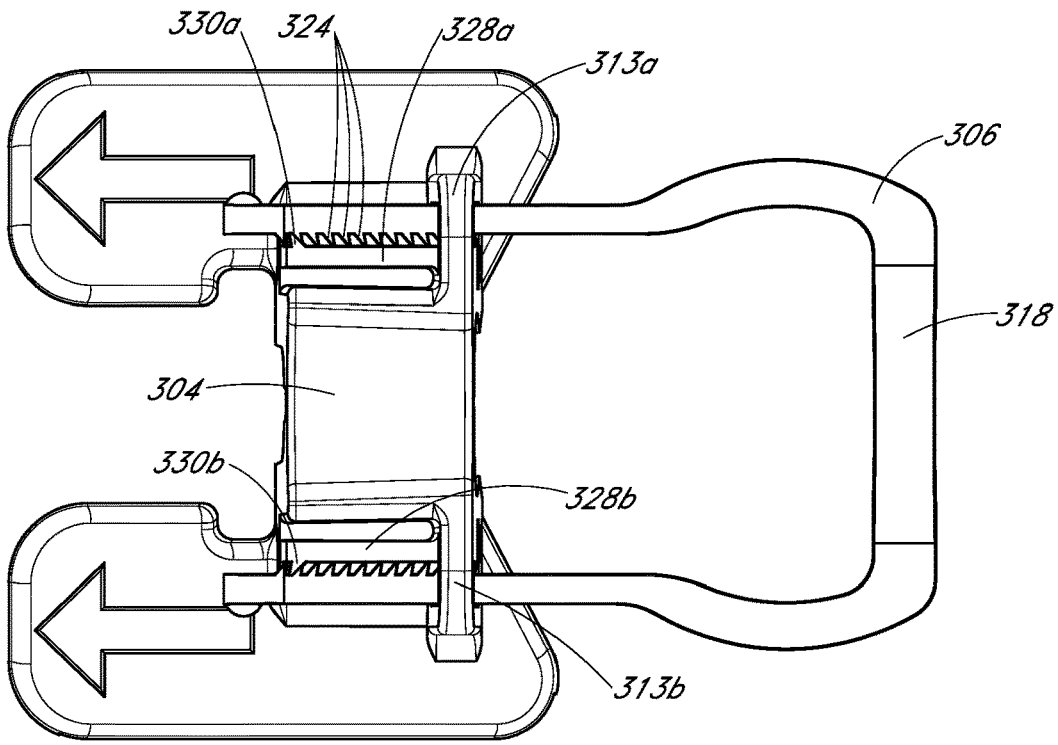
FIG. 29 is a top plan view of the clamp and retainer from FIG. 27 with arms of the clamp extending through corresponding slots in the retainer.
Figure 30:
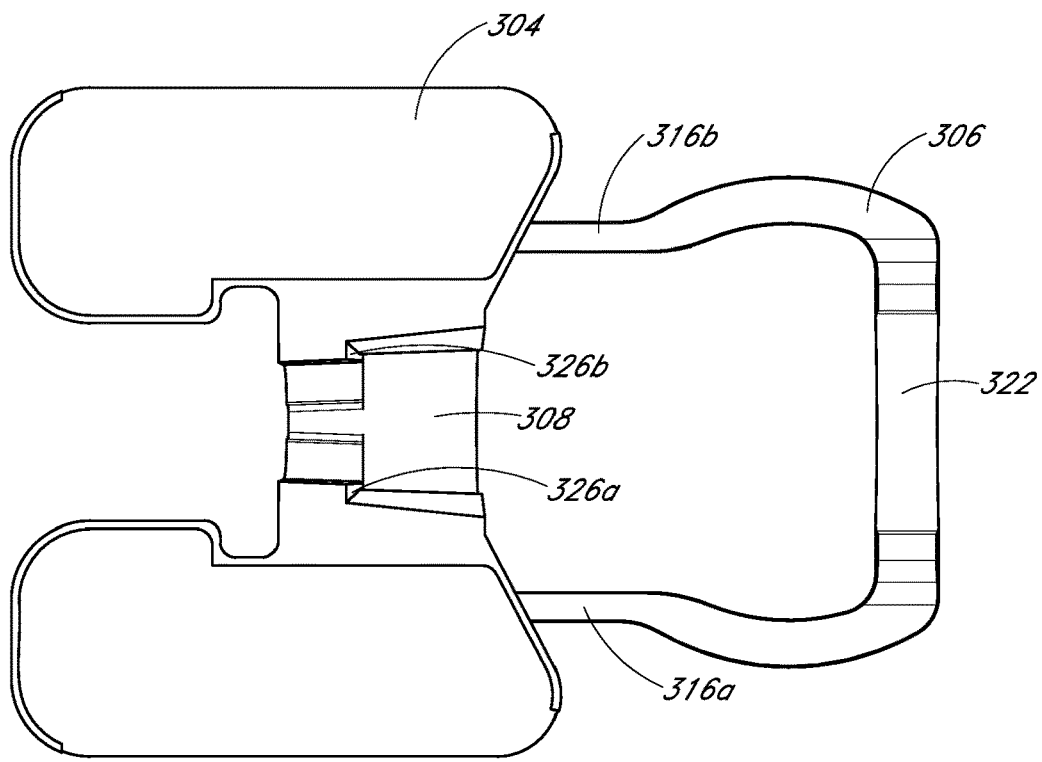
FIG. 30 is a bottom plan view of the clamp and retainer of FIG. 27 and shows a channel configured to receive a portion of a medical article.

FIGS. 29 and 30 are top and bottom plan views, respectively, of the clamp 306 and retainer 304 shown in FIG. 27. As can be seen in FIG. 30, the channel 308 includes a distally-facing abutment surface comprising two abutment surfaces 326(a), 326(b) separated by a narrow groove. At least one of the abutment surfaces 326(a), 326(b) is configured to abut a corresponding, proximally-facing surface of the medical article when the medical article is received in the channel 308 and when the clamp 306 is ratcheted toward the retainer 304, so as to inhibit longitudinal movement of the retained medical article in at least a proximal direction.

Figure 31:
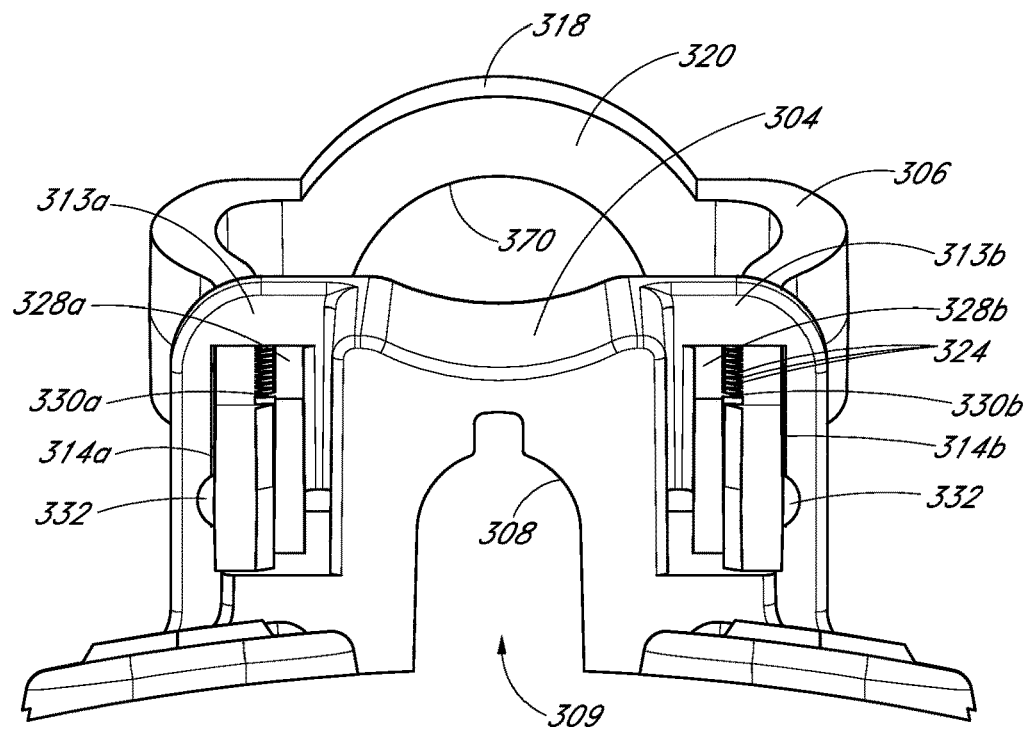
FIG. 31 is a front view of the clamp and retainer of FIG. 29.
Figure 32:
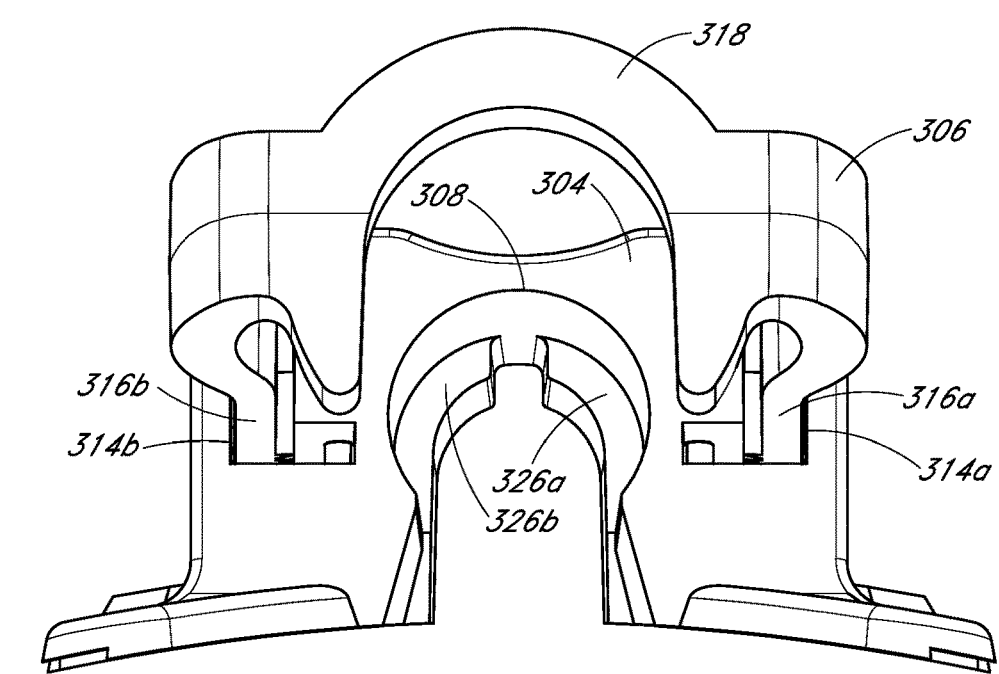
FIG. 32 is a rear view of the clamp and retainer of FIG. 29.
Figure 33:
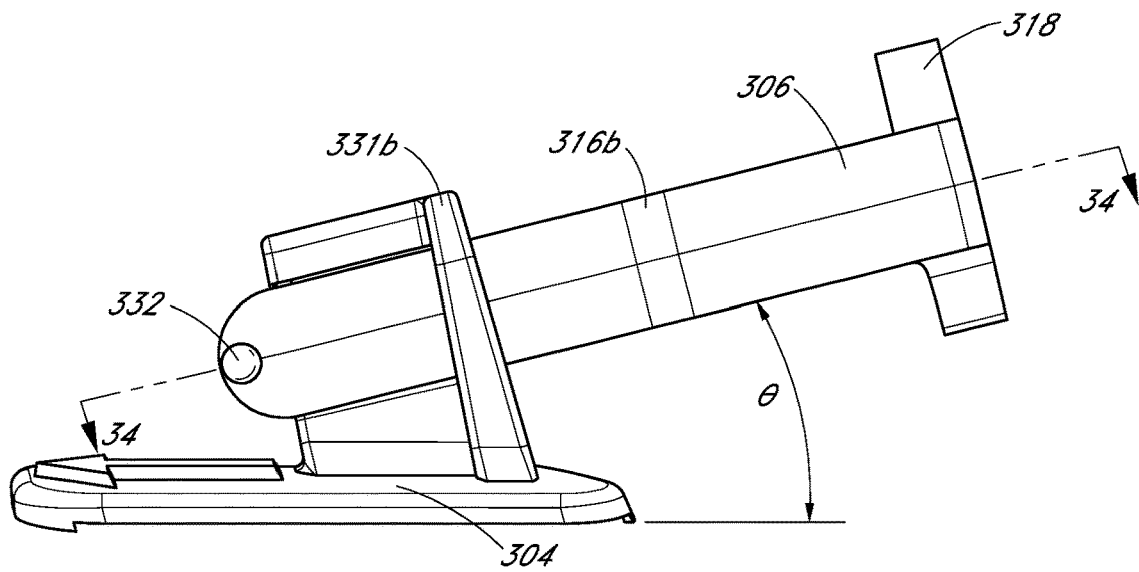
FIG. 33 is a side view of the clamp and retainer of FIG. 29.

FIGS. 31 through 33 show front, rear, and side views, respectively, of the clamp 306 and retainer 304 of FIG. 3. As most clearly shown in FIG. 33, an axis of the central channel 308 lies at an angle θ with respect to the base surfaces of the retainer 304. The desired angle θ between the medical article and the patient is created by angling the axis of the central channel 308. This angle is selected in order to align the axis of the channel 308 of the retainer with the desired incident angle with which the medical article is to contact the skin of the patient. A variety of different angles can be used, ranging from 0° to 45°, and more preferably from 5° to 25°. For instance, for the securement of intravenous catheters, it is desirable for the angle of incidence or 0 of the catheter to the skin of the patient to be between about 7° to about 15°. For the securement of arterial catheters, it is desirable for the angle of incident of the catheter to the skin of the patient to be about 12.5°. By angling the axis of the channel 308 at the desired angle θ, which will depend upon the particular securement application (e.g., securing an arterial catheter, an intravenous catheter, etc.), the proper angle of incidence for a catheter can be maintained.

Figure 34:
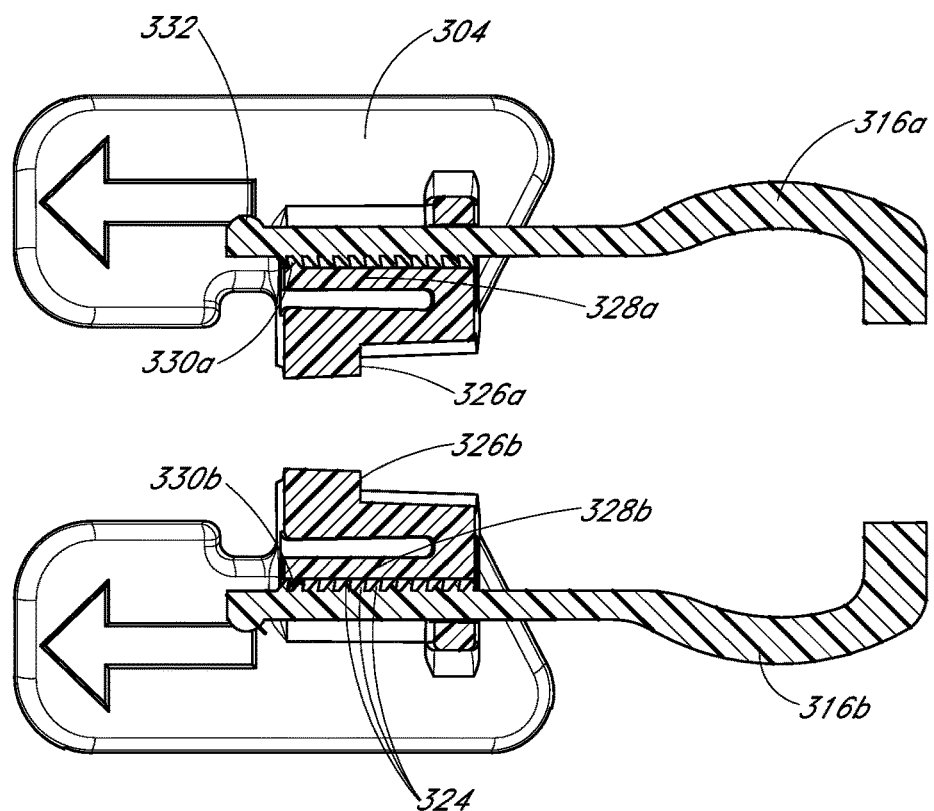
FIG. 34 is a cross-sectional view of the clamp and retainer taken through line 34-34 of FIG. 33 and shows beams defining a surface of the slots engaged with the arms of the clamp.

FIG. 34 is a top cross-sectional view through the securement system 300 of FIG. 33 and shows the teeth 324 of each clamp arm 316(a), 316(b) facing a laterally-extending locking tooth 330(a), 330(b) on the retainer 304. The clamp arms 316(a), 316(b) can be configured such that their proximal ends are spaced apart by a dimension slightly shorter than a dimension of the retainer 304. By such a configuration, the clamp arms 316(a), 316(b) can slightly pinch the retainer 304 when they are engaged with the retainer 304. The retainer 304 can optionally include one or more tracks or guides to help guide the clamp 306, and/or to help maintain the angle of the clamp 306 with respect to the insertion site, as the clamp 306 moves in a longitudinal direction.

As also illustrated in FIG. 34, the clamp 306 can include one or more stops 332 disposed at or near the proximal ends of the clamp arms 316(a), 316(b). The stops 332 can be configured to cooperate with one or more protrusions or surfaces on the retainer 304 (for example, proximally-facing surfaces of either or both wings 313(a), 313(b)) to inhibit longitudinal distal movement of the clamp beyond a particular position if or when the clamp 306 is loosened from the retainer 304.

Figure 35:
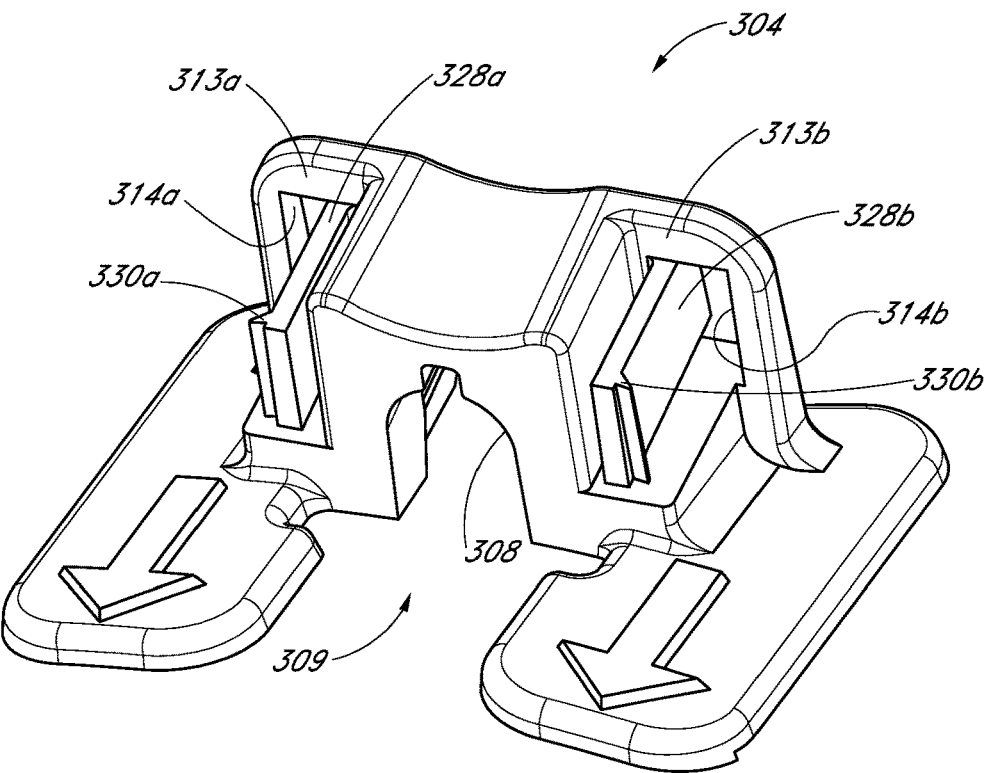
FIG. 35 is a front perspective view of the retainer from FIG. 29 without the clamp.
Figure 36:
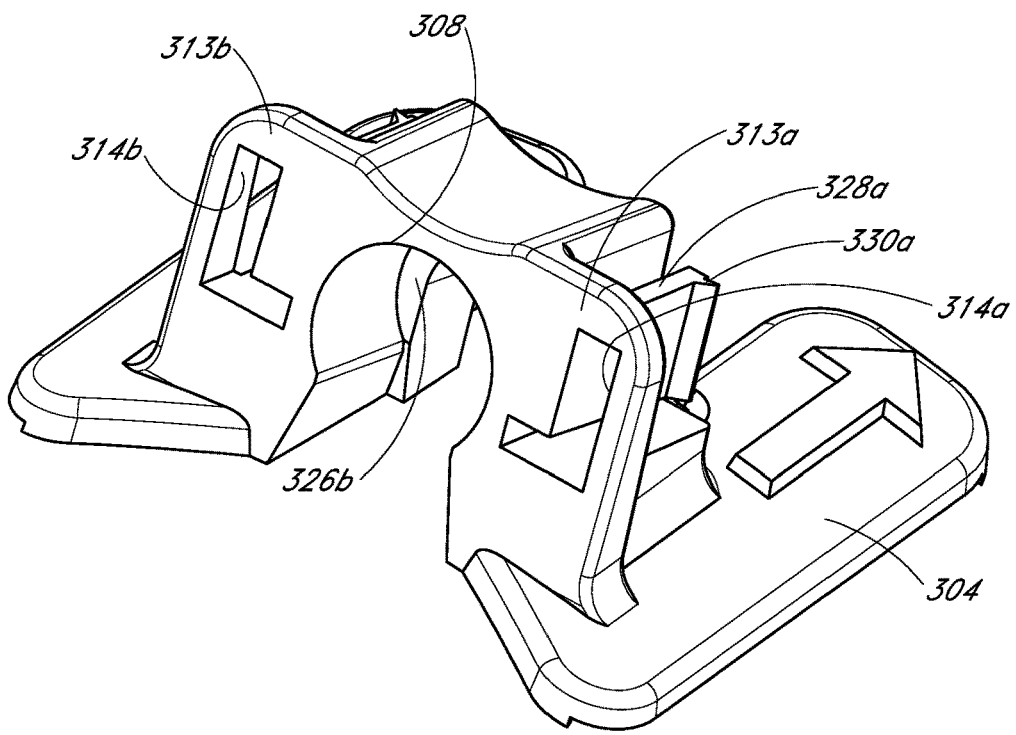
FIG. 36 is a rear perspective view of the retainer of FIG. 35.
Figure 37:
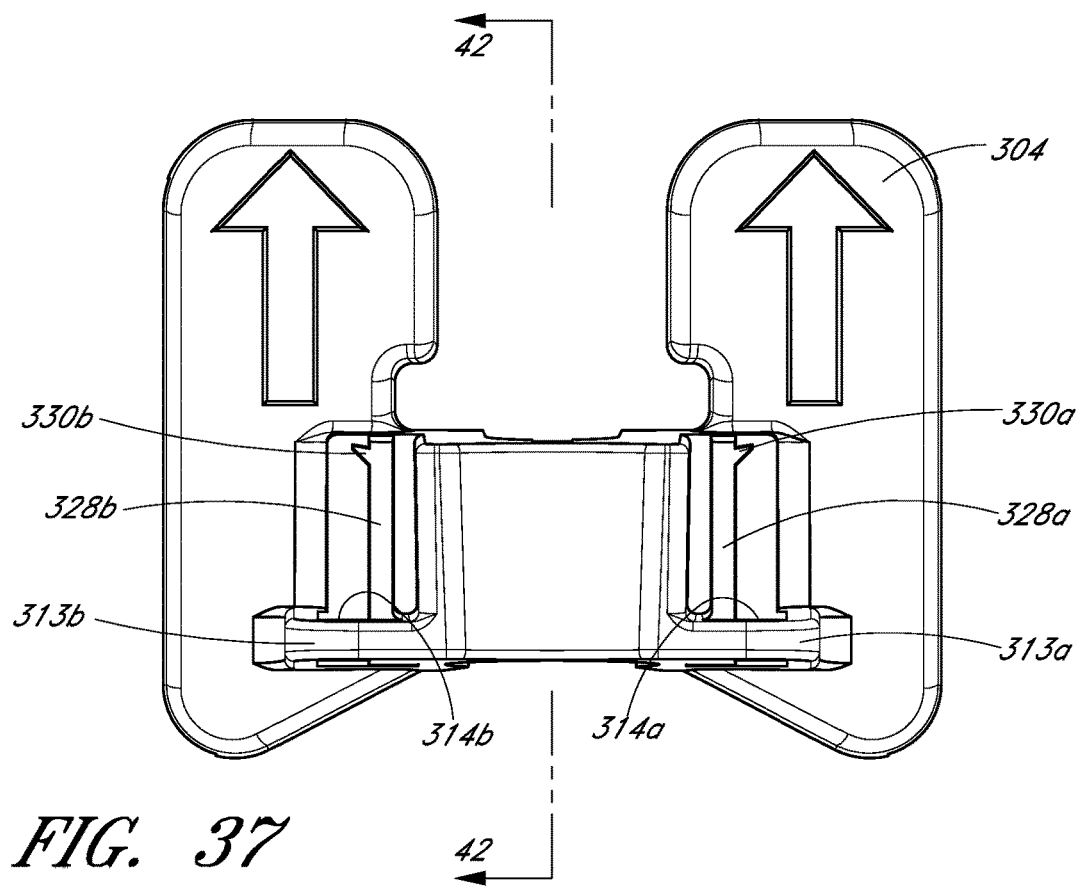
FIG. 37 is a top plan view of the retainer of FIG. 35.
Figure 38:
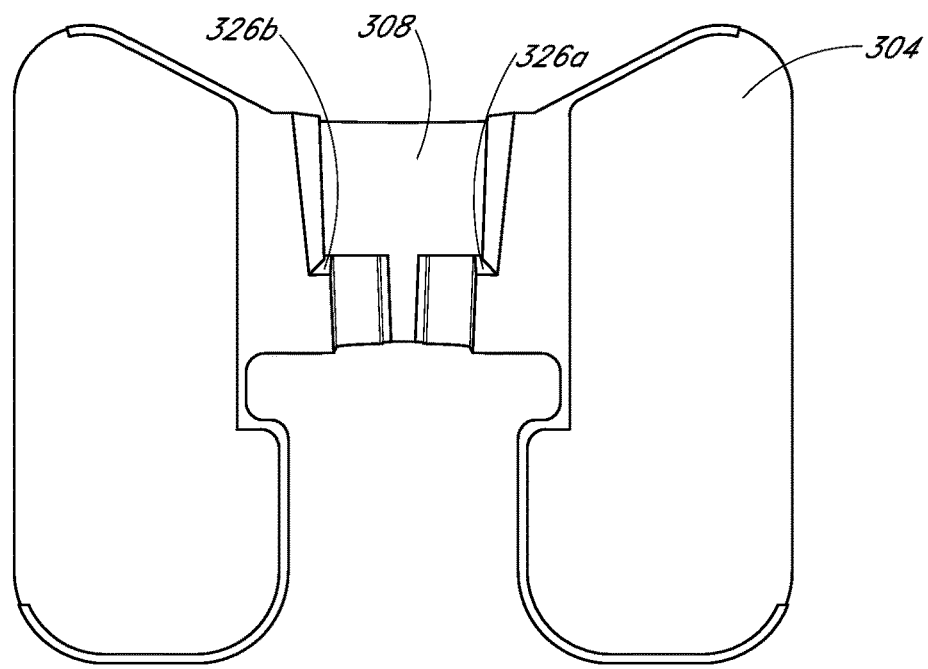
FIG. 38 is a bottom plan view of the retainer of FIG. 35.
Figure 39:
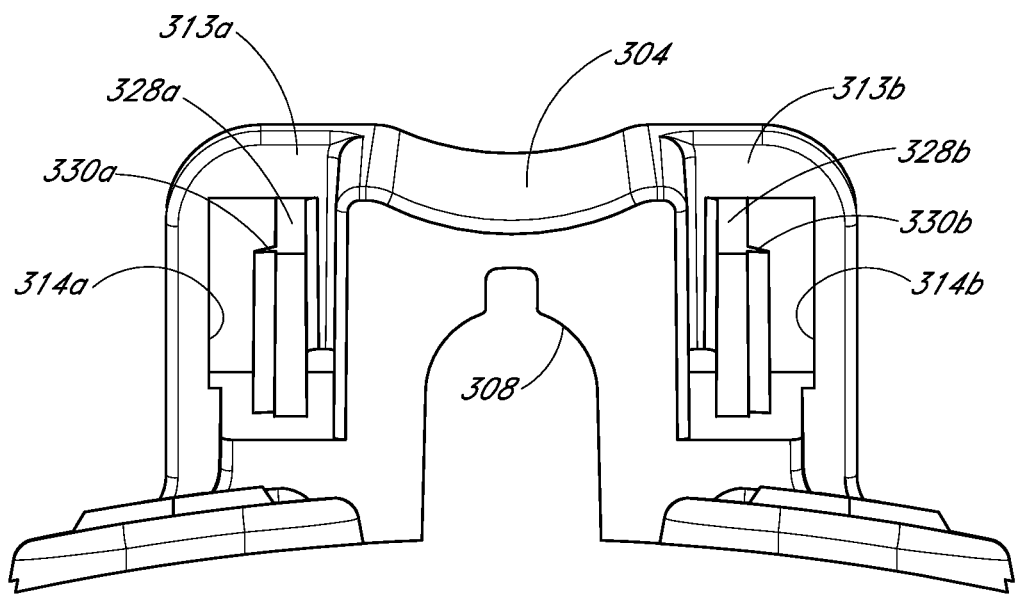
FIG. 39 is a front view of the retainer of FIG. 35.
Figure 40:
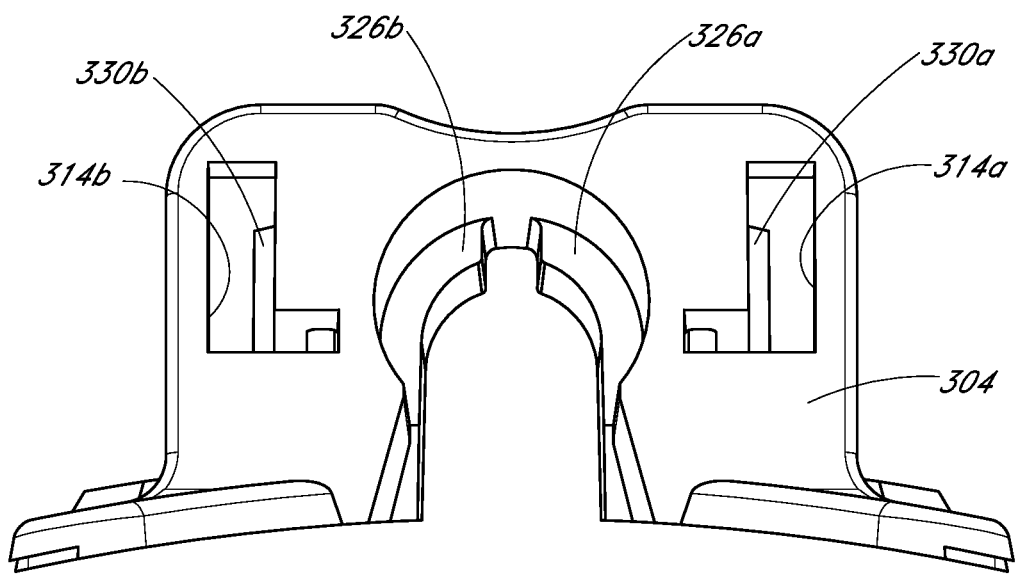
FIG. 40 is a rear view of the retainer of FIG. 35.
Figure 41:
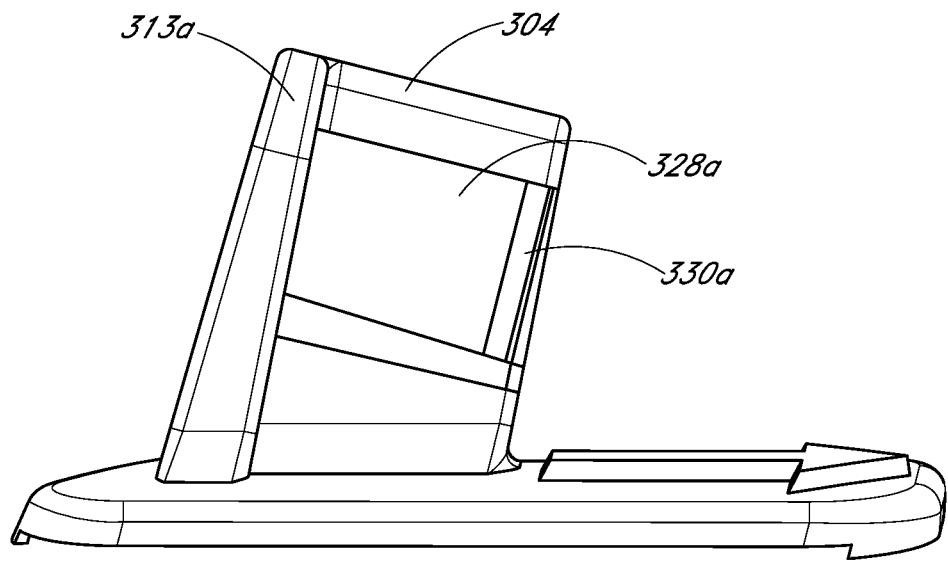
FIG. 41 is a side view of the retainer of FIG. 35.

FIGS. 35 and 36 show front and rear perspective views, respectively, of the retainer 304 of FIG. 29. FIGS. 37 and 38 show top and bottom plan views, respectively, of the retainer 304 of FIG. 29. FIGS. 39 through 41 show front, rear, and side views, respectively, of the retainer 304 of FIG. 29.

Figure 42:
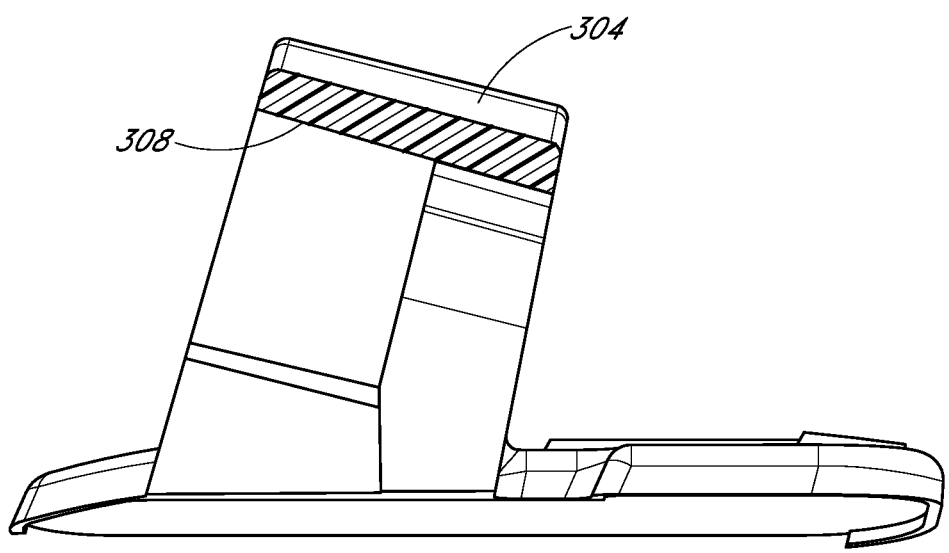
FIG. 42 is a cross-sectional view of the retainer taken through line 42-42 of FIG. 37, and shows an abutment surface configured to abut against a surface of a secured medical article.

FIG. 42 is a cross-sectional view of the retainer 304 taken through line 42-42 of FIG. 37 and shows an abutment surface 326(b) configured to abut against a surface of a secured medical article. Although the channel 308 can be formed in various shapes depending upon the desired application (e.g., depending upon a shape of the retained portion of the medical article for which the retainer is designed to be used), the channel 308 desirably has a sufficient length in the longitudinal direction to stabilize the connector fitting, catheter hub, or other medical article, rather than act as a fulcrum for the fitting. That is, the retainer 304 is configured to receive a sufficient length of the medical article to inhibit movement of the article in the lateral, longitudinal and transverse direction (i.e., to inhibit yaw, pitch and axial movement of the article).

Figure 43:
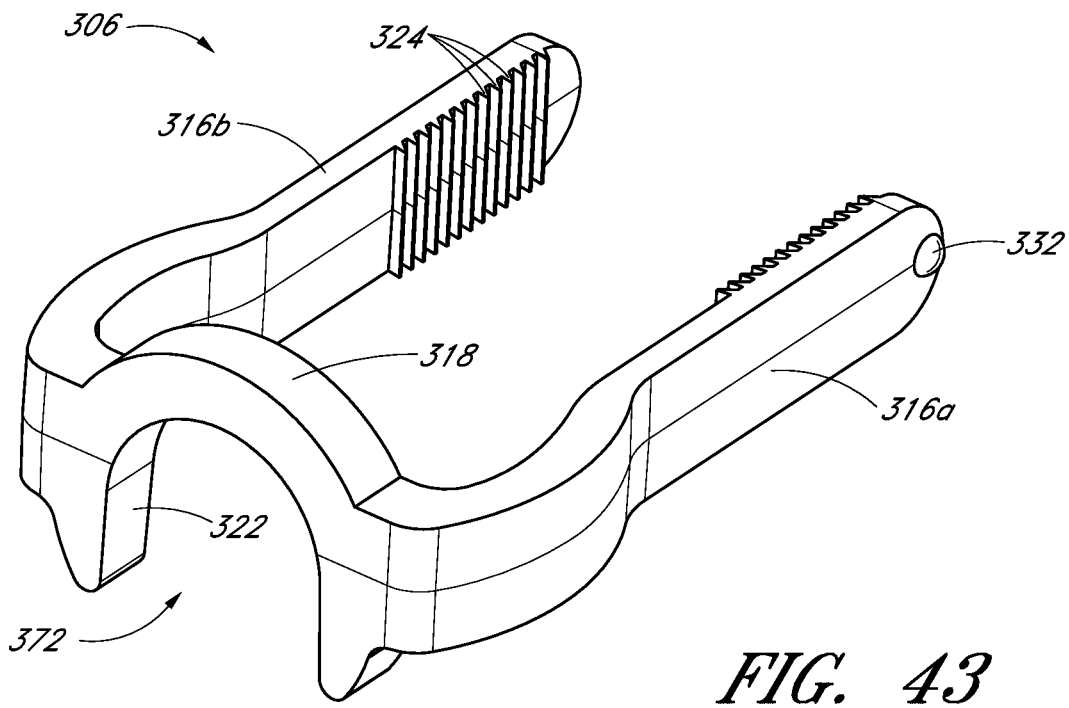
FIG. 43 is a top perspective view of the clamp from FIG. 29 without the retainer and shows a series of teeth on each arm that engage with the beams illustrated in FIG. 34.
Figure 44:
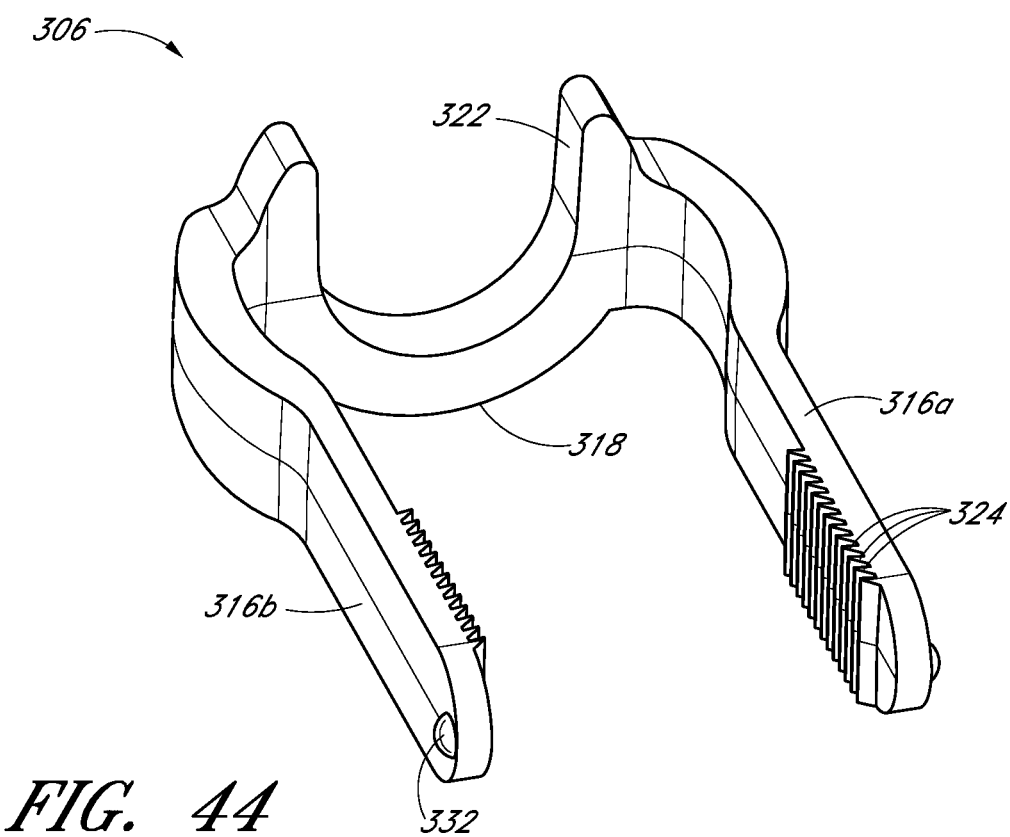
FIG. 44 is a bottom perspective view of the clamp of FIG. 43.

FIG. 43 is a top perspective view of the clamp 306 from FIG. 29 without the retainer 304 and shows a series of teeth 324 on each arm 316 that engage with the beam 328 illustrated in FIG. 34. FIG. 44 is a bottom perspective view of the clamp 306 of FIG. 29. As can be seen in these figures, the clamp 306 can include one or more protrusions or motion stops 332 configured to cooperate with a corresponding surface of the retainer 304 to inhibit longitudinal movement of the clamp 306 beyond a particular position (in the distal direction) when the clamp 306 is loosened from the retainer 304. Such an arrangement can serve to keep the clamp 306 and the retainer 304 from completely separating from one another even after they are loosened from one another.

Figure 45:
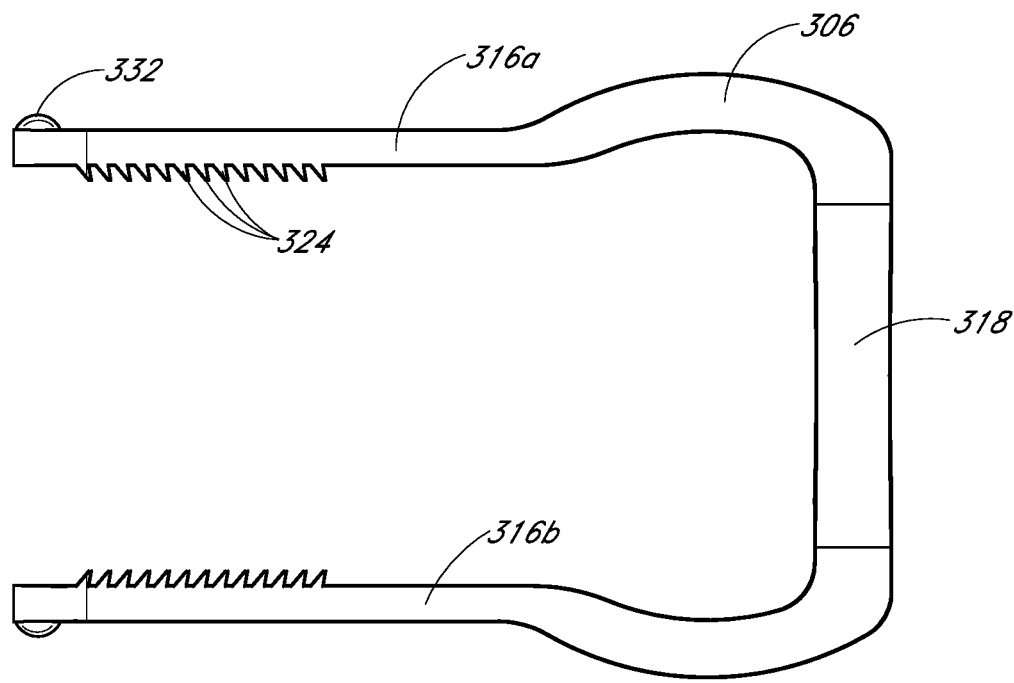
FIG. 45 is a top plan view of the clamp of FIG. 43 and shows an outwardly extending protrusion on each arm that cooperates with a stop in the slot of the retainer to inhibit longitudinal proximal movement of the clamp beyond a particular position during fabrication, assembly and shipping.
Figure 46:
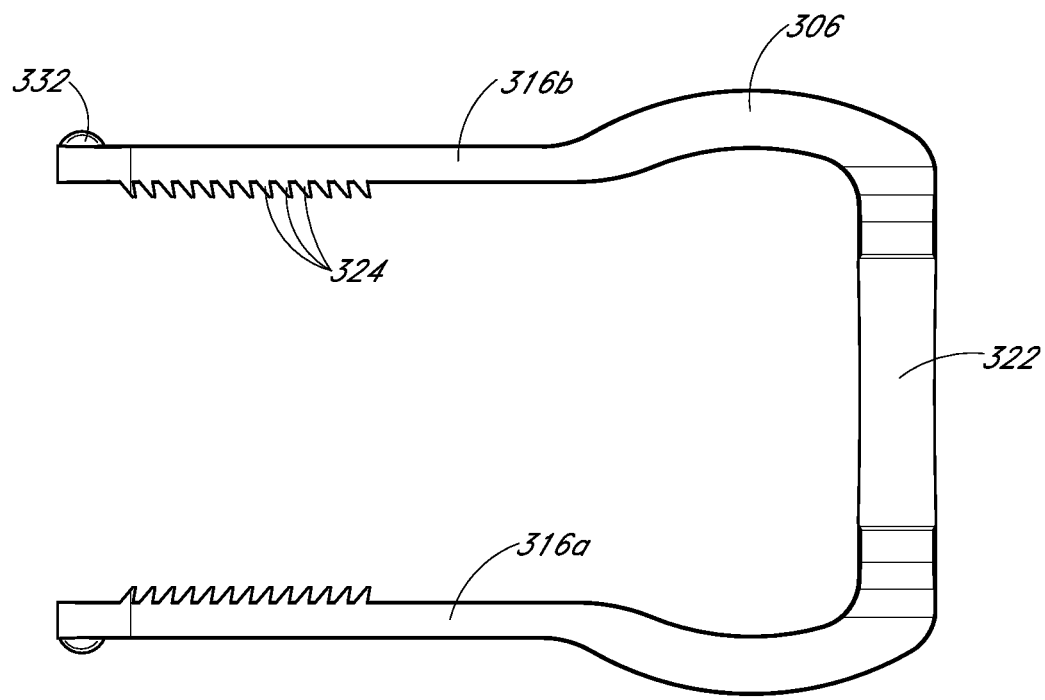
FIG. 46 is a bottom plan view of the clamp of FIG. 43.
Figure 47:
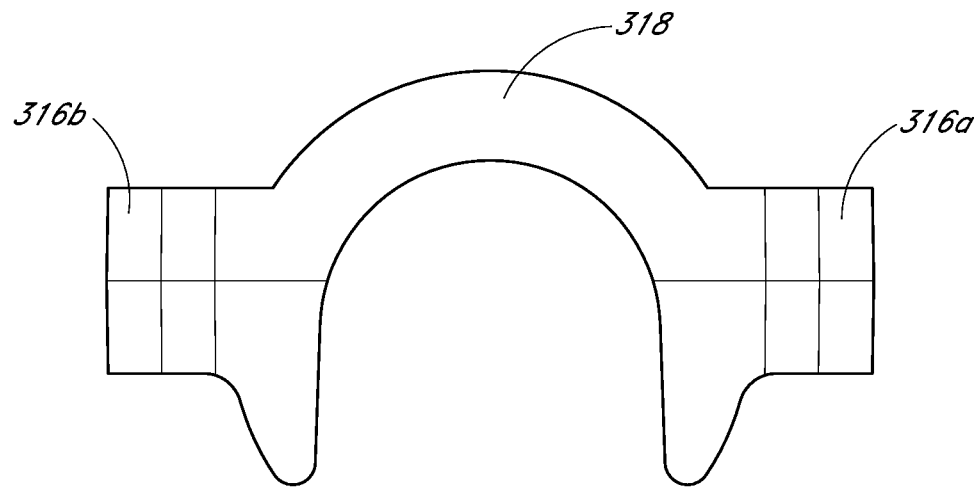
FIG. 47 is a rear view of the clamp of FIG. 43 and shows a collar disposed so as to abut a distal facing surface of a secured medical article.
Figure 48:
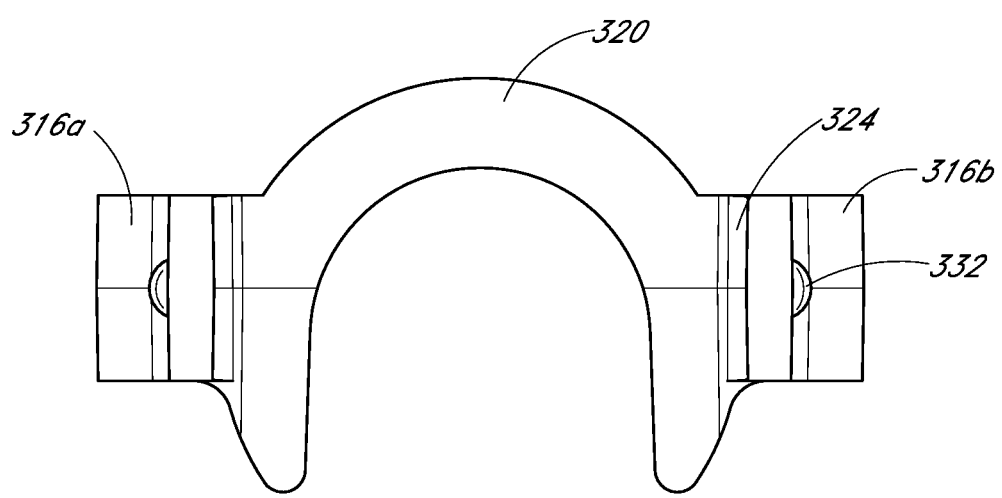
FIG. 48 is a front view of the clamp of FIG. 43.

FIGS. 45 and 46 are top and bottom plan views, respectively, of the clamp of FIG. 43 and show the inwardly extending ratchet teeth 324 and the outwardly extending motion stop 332 on each clamp arm 316(a), 316(b). FIG. 46 shows the inwardly-facing surface 322 of the clamp 306. FIGS. 47 and 48 are rear and front views, respectively, of the clamp 306 of FIG. 43 and show the collar 318 disposed so as to abut a surface of a secured medical article. FIG. 48 shows the proximally-facing surface 320 of the clamp 306.

Figure 49:
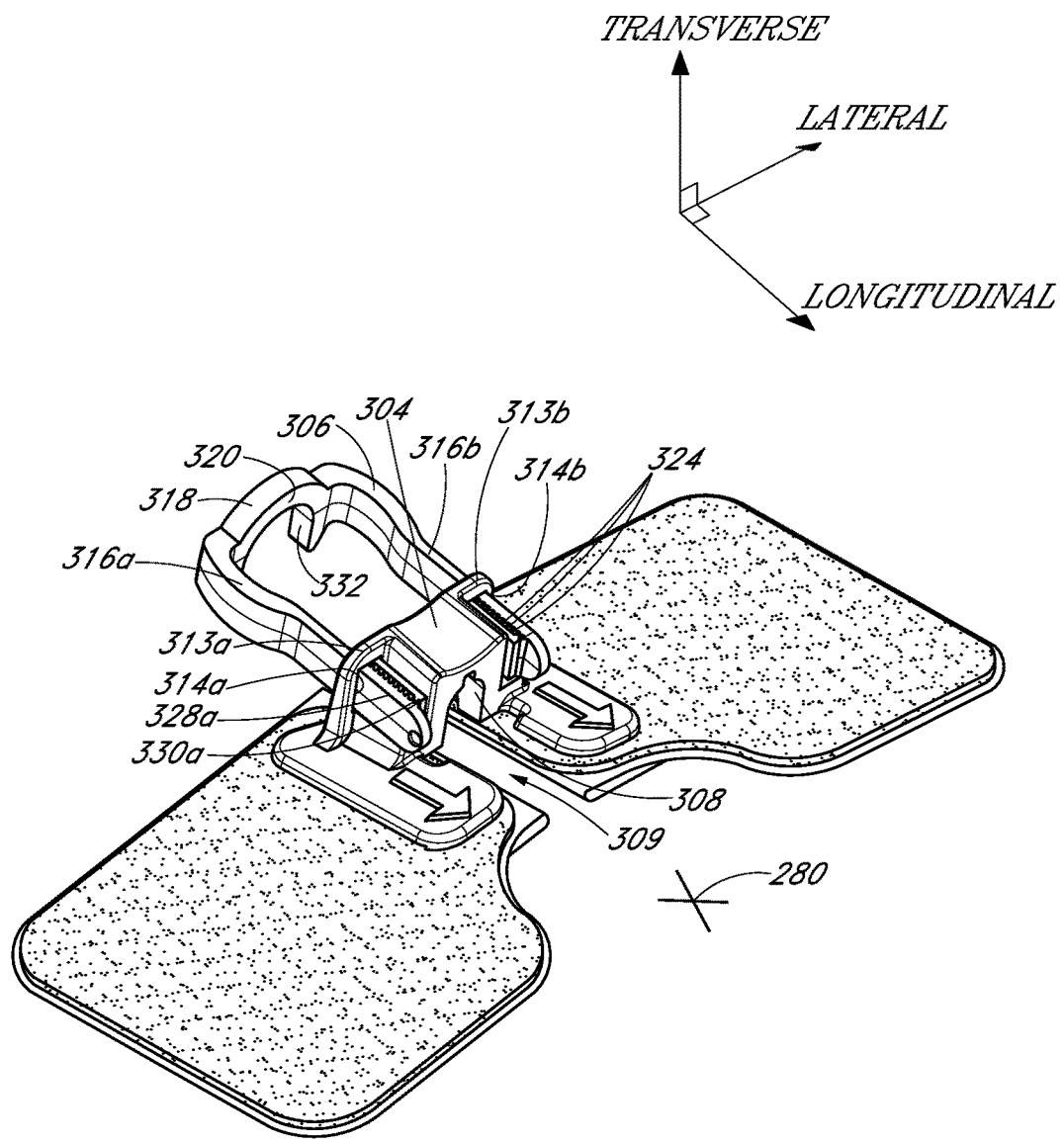
FIG. 49 is an exploded perspective view of the securement system shown in FIG. 27 prior to inserting an exemplary medical article.

FIG. 49 is an exploded perspective view of the embodiment shown in FIG. 27, shown with an exemplary medical article 302 prior to being received in the retainer 304. As can be seen in FIG. 49, the access opening of the collar 118 is aligned with the access opening 308 of the retainer 304 along the longitudinal axis, to allow placement of proximal and distal portions of the medical article 302 in the securement system 300. The medical article 302 includes a catheter hub 360 having a stepped-taper profile and a connector fitting 362 including a spin nut 364. The illustrated medical article has a proximally-facing surface 350, a distally-facing surface 352, and an outwardly-facing surface 354. In the illustrated embodiment, the step in the taper of the catheter hub 360 forms the proximally-facing abutment surface 350. The rear surface of the spin nut 364 forms the distally-facing surface 352, and the outer surface of the distal portion of the connector fitting 362 forms the outwardly-facing surface 354. Alternatively or in addition, the tapered surfaces of the catheter hub 360 can act as an abutment surface. For example, the channel 308 forms a stepped taper that generally corresponds to the stepped taper of the catheter hub 360 of the medical article 302. Thus, when the medical article 302 is placed in the securement system 300, the abutment surfaces 326(a), 326(b), as well as the inner tapering surfaces of the channel 308 (see FIG. 38), serve to inhibit longitudinal movement of the medical article in the proximal direction.

In embodiments in which at least a portion of the catheter hub has a tapered profile, an inner surface of the tapered channel alone can act as an abutment surface. In embodiments in which the catheter hub has a generally cylindrical profile, the retainer channel can include an inwardly-extending protrusion or ridge, a tapering or stepped inner surface, or any other suitable structure configured to abut the corresponding surface(s) of the catheter hub and inhibit longitudinal movement of the medical article in the proximal direction.

Figure 50:
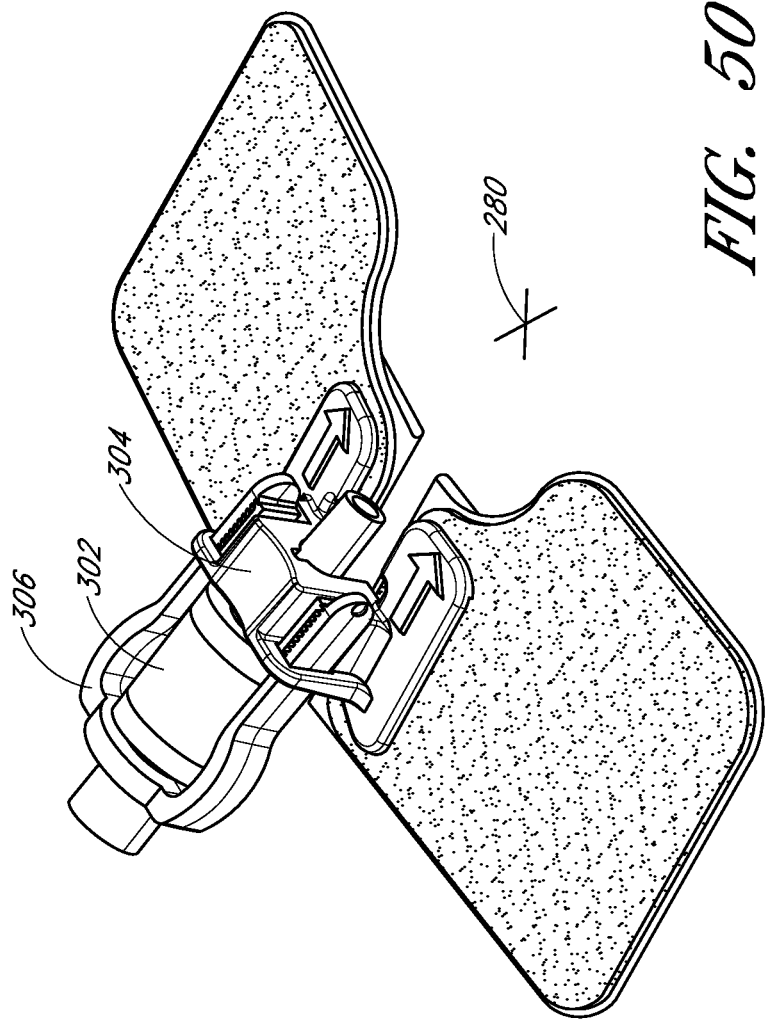
FIG. 50 is a view similar to FIG. 49 except that the medical article is received in a channel of the retainer.

FIG. 50 shows the exemplary medical article 302 received in the channel 308 of the retainer 304, with the clamp arms 316(a), 316(b) engaged with the retainer 304 but prior to advancement of the arms 316(a), 316(b). In this position, the abutment surfaces 326(a), 326(b) inside the channel 308 (see FIG. 30) cooperate with the proximally-facing surface 350 of the medical article 302 to inhibit longitudinal movement of the article 302 in a proximal direction (toward the insertion site 380) beyond a desired position.

Figure 51:
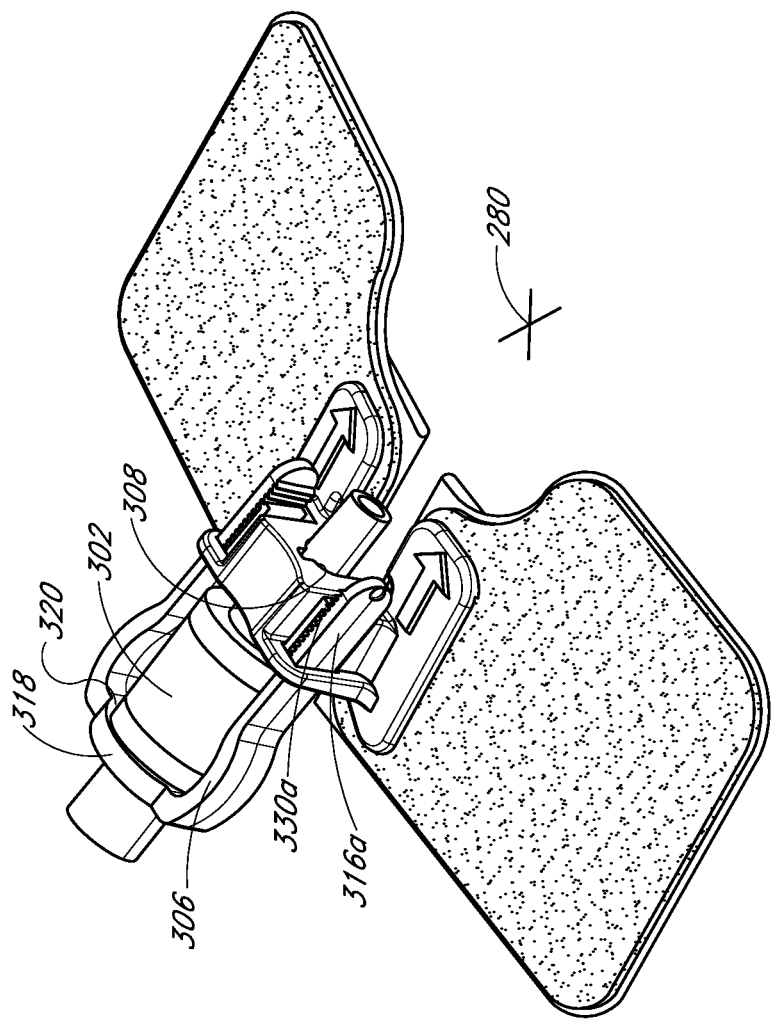
FIG. 51 is a view similar to FIG. 50 except that the clamp is advanced in a proximal direction toward the retainer to secure the medical article therebetween and inhibit movement of the medical article in both the proximal and distal directions

FIG. 51 shows the clamp 306 engaged with the retainer 304, with the two parts tightened together about the medical article 302. The collar 318 partially surrounds a distal portion of the medical article 302. In the illustrated secured position, the proximally-facing surface 320 of the collar 318 cooperates with the distally-facing surface 352 of the medical article 302 to inhibit longitudinal movement of the article 302 in a distal direction beyond a desired position, and the inwardly-facing surface 322 of the collar 318 cooperates with the outer surface 354 of the medical article 302 to inhibit both lateral and transverse movement of the medical article 302.

The securement system 300 illustrated in FIGS. 27-34 includes a mechanism by which the clamp 306 may be easily retracted from the retainer 304 after the clamp 306 and retainer 304 have been tightened about a medical article. As can be seen in FIG. 51, the distal ends of the clamp arms 316(a), 316(b) include sections which are curved or bent laterally outward. A medical provider can release the clamp 306 from the retainer 304 by pinching on the curved portions, thereby causing the proximal ends of the clamp arms 316(a), 316(b) to pivot about the distal ends of the retainer and separating the ratchet teeth 324 from the locking teeth 330(a), 330(b).

Although the embodiment illustrated in FIGS. 27-34 includes ratchet teeth on the clamp arms and locking teeth on the retainer, alternative embodiments can of course include a reverse configuration in which ratchet teeth are provided on the retainer and one or more locking teeth are provided on an arm or arms of the clamp. Of course, the clamp and the retainer can include any other suitable corresponding structure that allows relative motion of the clamp and the retainer in a longitudinal direction, while providing securement of their relative positions as desired.

Figure 52:
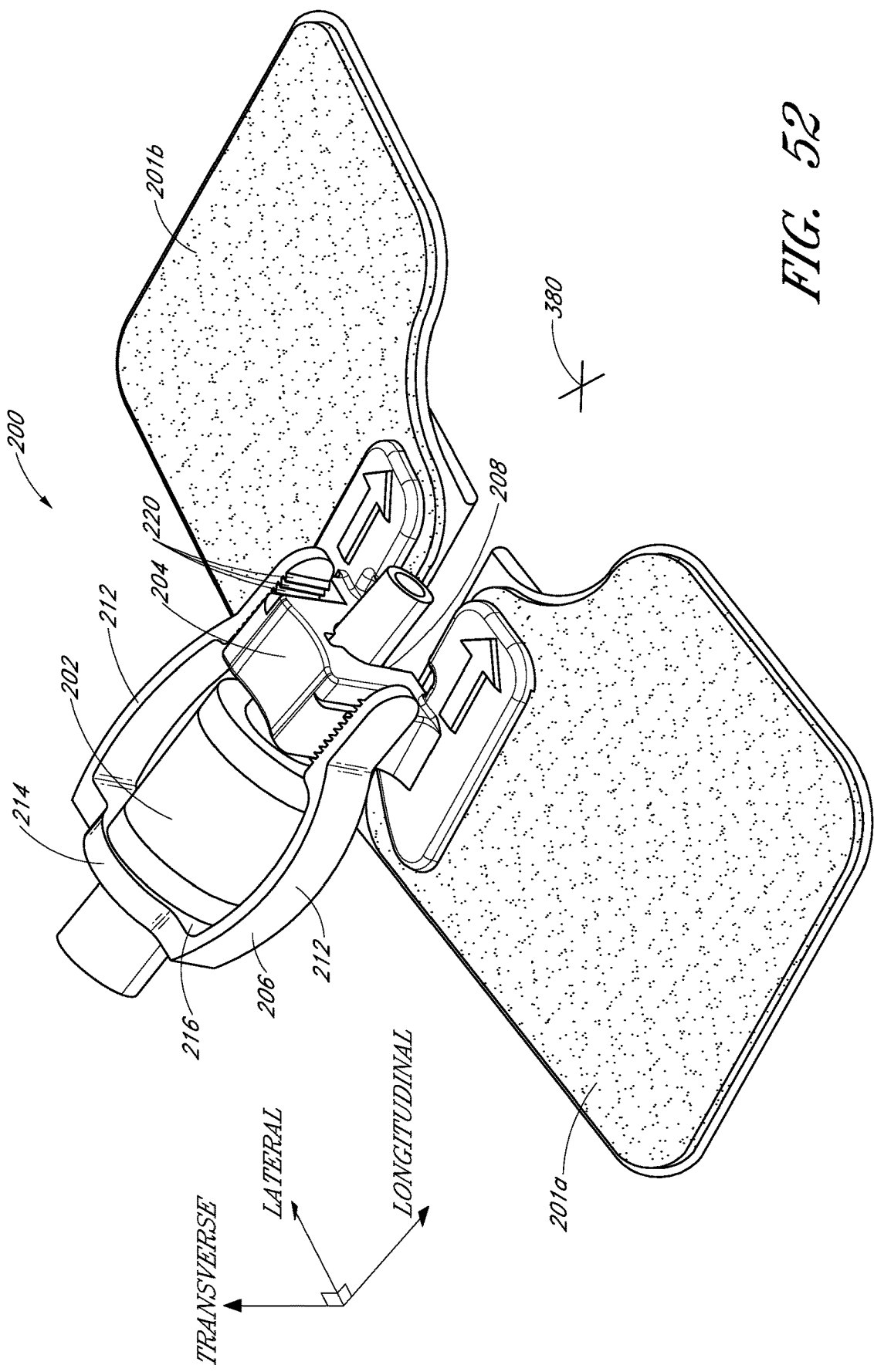
FIG. 52 is a perspective view of a securement system according to another preferred embodiment of the present invention, illustrating a cooperating clamp and retainer supported by a pair of anchor pads securing an exemplary medical article.
Figure 53:
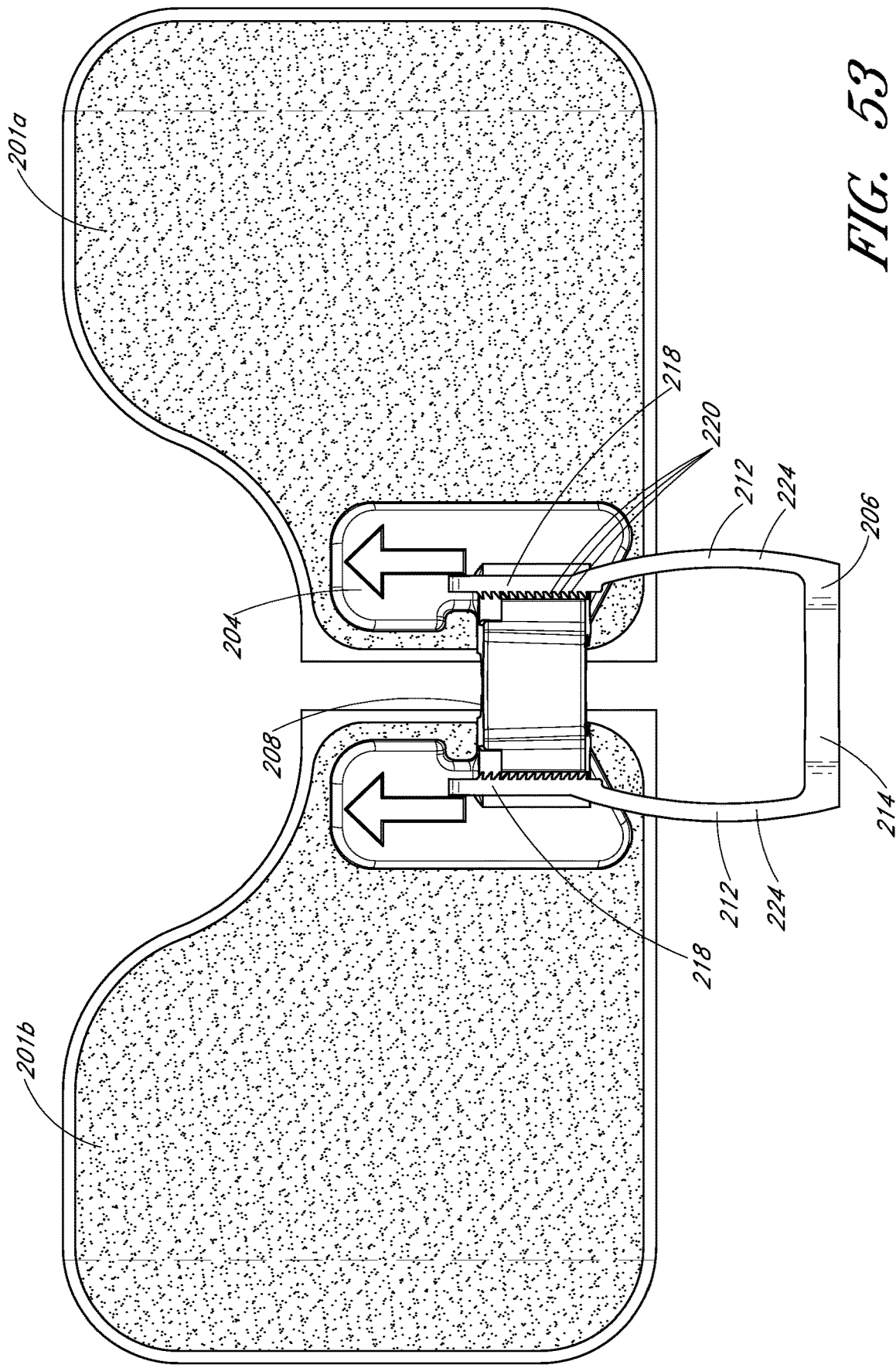
FIG. 53 is a top plan view of the securement system illustrated in FIG. 52, shown without the medical article.
Figure 54:
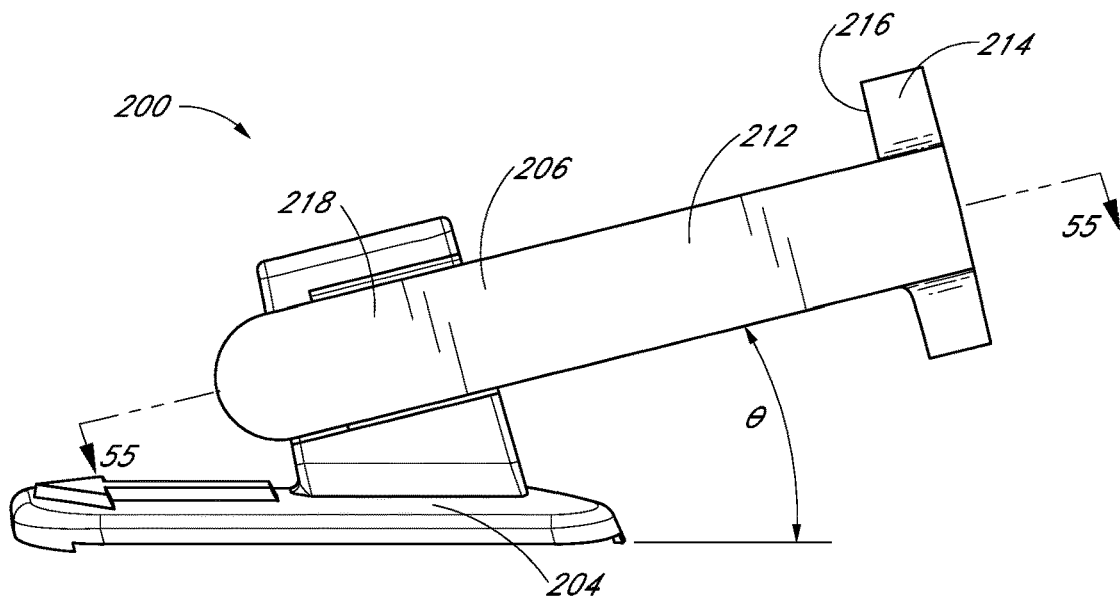
FIG. 54 is a side view of the clamp and retainer of FIG. 53 without the anchor pads.
Figure 56:
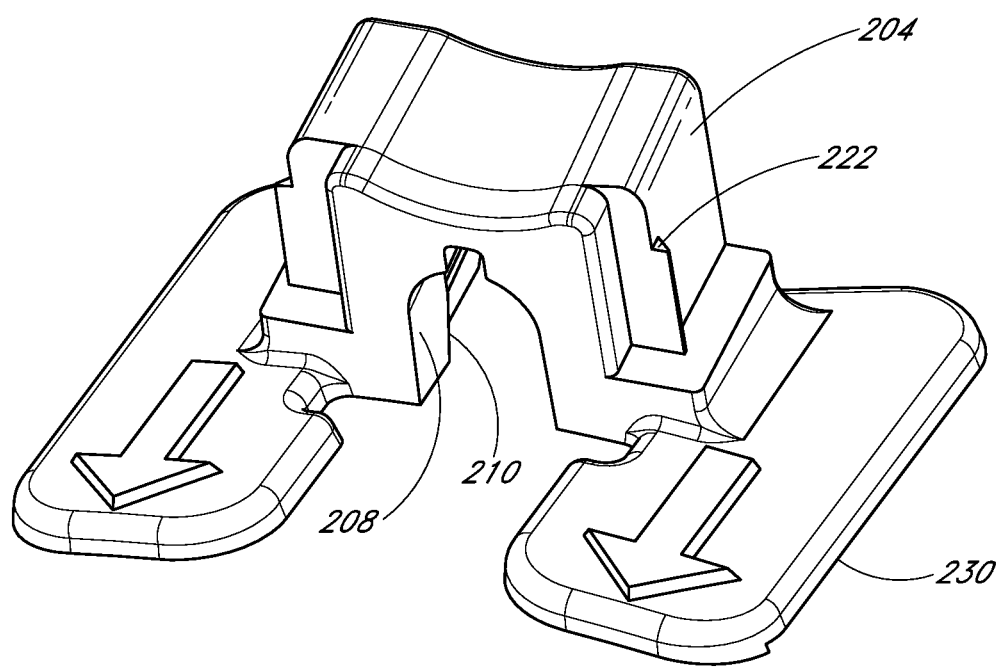
FIG. 56 is a front perspective view of the retainer from FIG. 54 with the clamp removed.

FIG. 52 is a perspective view of a securement system 200 and medical article 202 according to another preferred embodiment of the present invention and shows another interengagement structure between the arms 212 of the clamp 206 and the retainer 204 that differs from that which is shown in FIG. 1. The system 200 is shown with anchor pads 201(a), 201(b) and is illustrated securing an exemplary medical article 202. The securement system 200 includes a retainer 204 and a clamp 206. A portion of the retainer 204 forms a channel 208 which is configured to receive at least a portion of the medical article 202 prior to the securement system 200 being attached to the skin of a patient near an insertion site 280 (indicated by an "X" in FIG. 52). The clamp 206 includes two clamp arms 212 that are connected at a distal portion of the clamp 206 by a collar 214. A plurality of vertically-extending ratchet teeth 220 are disposed on proximal ends 218 of the clamp arms 212, on inward-facing surfaces of the clamp arms 212. FIG. 53 is a top plan view of the system 200 shown without the medical article 202, and better illustrates the profile of the clamp arms 212 and the ratchet teeth 220. As can be seen in FIG. 54, in the illustrated embodiment, the clamp 206 is configured to engage with the retainer 204 so that it sits at an angle θ (which may be, for example, about 7°) with respect to a lower surface 230 of the retainer (see FIG. 56) and thus, with respect to an insertion site on the skin of the patient. The illustrated clamp 206 is also configured to engage with the retainer 204 so that the clamp arms 212 are generally aligned with a central axis of the channel 208. In other embodiments, all or portions of the clamp can be configured to engage with the retainer so that the clamp extends at any other angle with respect to the lower surface of the retainer, and/or with respect to an axis of the retainer channel.

Figure 55:
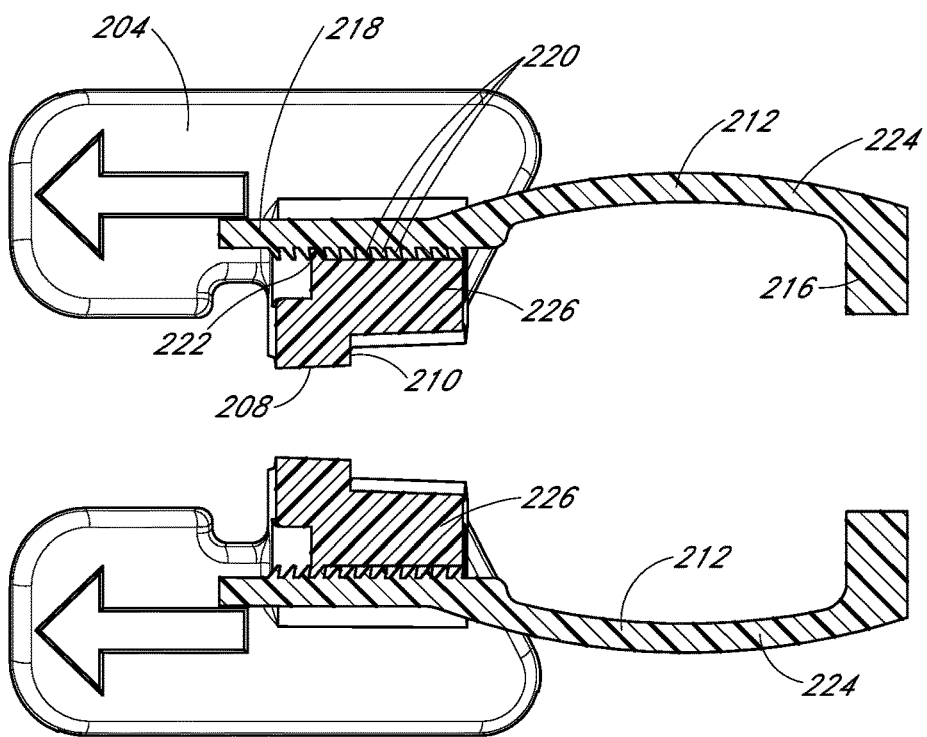
FIG. 55 is a cross-sectional view of the clamp and retainer of FIG. 54 taken through line 55-55 of FIG. 54 and shows beams the engagement of the arms of the clamp with the retainer.

FIG. 55 is a top cross-sectional view through the securement system 200 of FIG. 54 and shows the teeth 220 of each clamp arm 212 facing a laterally-extending protrusion 222 on the retainer 204. As can also be seen in FIG. 55, the channel 208 includes at least one distally-facing abutment surface 210. The distally-facing abutment surface 210 is configured to cooperate with a corresponding surface of the medical article 202 so as to inhibit movement of the medical article 202 beyond a desired proximal position. The collar 214 includes at least one proximally-facing abutment surface 216 which is configured to cooperate with a corresponding surface of the medical article 202 so as to inhibit movement of the medical article 202 beyond a desired distal position. The collar 214 also includes at least one inward-facing (and/or downward-facing) surface which is configured to cooperate with a corresponding outer (and/or upper)

surface of a portion of the medical article 202 so as to inhibit movement of the medical article 202 in a lateral and/or transverse direction when the clamp 206 is engaged with the retainer 204.

The proximal ends 218 of the clamp arms 212 can be generally straight sections which are provided with vertically-oriented ratchet teeth 220. The ratchet teeth 220 cooperate with laterally-extending protrusions 222 on the retainer 204 (see FIG. 56) to engage the clamp 206 with the retainer 204 and set the longitudinal position of the clamp 206 with respect to the retainer 204. The clamp arms 212 can be configured such that their proximal ends 218 are spaced apart by a dimension slightly shorter than a dimension of the retainer 204. By such a configuration, the clamp arms 212 slightly pinch the retainer 204 when they are engaged with the retainer 204. The retainer 204 can optionally include one or more vertically-oriented tracks or guides to help guide the clamp 206, and/or to help maintain the angle of the clamp 206 with respect to the insertion site, as the clamp 206 moves in a longitudinal direction.

The distal ends 224 of the clamp arms 212 can include sections which are curved or bent laterally outward. A medical provider can release the clamp 206 from the retainer 204 by pinching on the curved portions, thereby causing the proximal ends 218 of the clamp arms to pivot about the distal ends 226 of the retainer and separating the ratchet teeth 220 from the protrusion 222.

In these and other embodiments, the retainer and/or the clamp can comprise two separate molded parts. The retainer and clamp can be tethered together or otherwise coupled, if so desired. The retainer and clamp can comprise any suitable material offering the desired degree of rigidity (and flexibility) for each part, including, without limitation, a stiff but somewhat flexible plastic, such as a polycarbonate. The anchor pads can comprise any suitable material, including, without limitation, paper, foam, or a flexible fabric such as tricot as described above.

The various embodiments of securement devices and techniques described above thus provide a number of ways to provide safe and stable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above.

What is claimed is:

1. A device for securing a medical article to a patient, comprising:
    a retainer, comprising:
        a body having a channel configured to retain at least a first portion of the medical article, the channel separating a first side of the body from a second side of the body, the first side of the body including a first slot, the second side of the body including a second slot;
        a first support member connected to the first side of the body;
        a second support member connected to the second side of the body; and
        a first abutment surface configured to abut a first surface of the medical article and inhibit longitudinal movement of the medical article in a first longitudinal direction; and
    a clamp comprising:
        a collar configured to at least partially surround at least a second portion of the medical article;
        a first arm connected to a first side of the collar, the first arm configured for insertion into the first slot;
        a second arm connected to a second side of the collar, the second arm configured for insertion into the second slot, wherein the second arm is parallel to the first arm, and wherein a longitudinal axis of the first arm and a longitudinal axis of the second arm are both parallel to a longitudinal axis of the channel; and
        a second abutment surface configured to abut a second surface of the medical article and inhibit longitudinal movement of the medical article in a second longitudinal direction opposite the first longitudinal direction.

2. The device according to claim 1, wherein the channel has a tapering inner shape which substantially aligns with a tapering outer shape of the first portion of the medical article, the tapering inner shape of the channel inhibiting movement of the medical article in the first longitudinal direction.

3. The device according to claim 1, wherein the first arm includes a first plurality of ratchet teeth, and wherein the first slot includes a first locking tooth, the first plurality of ratchet teeth configured for engagement with the first locking tooth.

4. The device according to claim 3, wherein the second arm includes a second plurality of ratchet teeth, and wherein the second slot includes a second locking tooth, the second plurality of ratchet teeth configured for engagement with the second locking tooth.

5. The device according to claim 4, wherein the first plurality of ratchet teeth and the second plurality of ratchet teeth extend toward the channel when the first arm is inserted into the first slot and the second arm is inserted into the second slot.

6. The device according to claim 3, wherein the first arm includes a first protrusion, and wherein the first slot includes a first motion stop, the first protrusion cooperating with the first motion stop to inhibit movement of the clamp in the first longitudinal direction.

7. The device according to claim 6, wherein the first plurality of ratchet teeth extend from a first side of the first arm, and wherein the first protrusion extends from a second side of the first arm different from the first side.

8. The device according to claim 7, wherein the first protrusion extends toward the channel when the first arm is inserted into the first slot.

9. The device according to claim 6, wherein the second arm includes a second protrusion, and wherein the second slot includes a second motion stop, the second protrusion cooperating with the second motion stop to inhibit movement of the clamp in the first longitudinal direction.

10. The device according to claim 1, further comprising a first anchor pad spaced a first width from a second anchor pad, wherein the first support member is positioned on the first anchor pad, wherein the second support member is positioned on the second anchor pad, and wherein the first arm is spaced from the second arm a second width greater than the first width.

11. The device according to claim 1, further comprising a first anchor pad spaced apart from a second anchor pad, wherein the first support member is positioned on the first anchor pad, and wherein the second support member is positioned on the second anchor pad.

12. The device according to claim 11, wherein the retainer further comprises a first arrow on the first support member, and a second arrow on the second support member, the first arrow and the second arrow pointing in a direction of an insertion site for the patient.

* * * * *